United States Patent
Chapuis et al.

[11] Patent Number: 5,118,865
[45] Date of Patent: Jun. 2, 1992

[54] CYCLIC KETONES AND THEIR USE AS PERFUMING INGREDIENTS

[75] Inventors: Christian Chapuis, Mies; Karl-Heinrich Schulte-Elte, Onex; Hervé Pamingle, Versoix; Christian Margot, Bassins, all of Switzerland

[73] Assignee: Firmenich SA, Geneva, Switzerland

[21] Appl. No.: 667,702

[22] Filed: Mar. 11, 1991

[30] Foreign Application Priority Data

Mar. 26, 1990 [CH] Switzerland .................... 00997/90

[51] Int. Cl.$^5$ .............................................. C07C 49/29
[52] U.S. Cl. .................................... 568/376; 568/377; 568/446; 512/22; 549/546
[58] Field of Search .................... 568/376, 377; 512/22

[56] References Cited

U.S. PATENT DOCUMENTS

| | | | |
|---|---|---|---|
| 3,057,913 | 10/1962 | Guex et al. | 568/377 |
| 3,928,645 | 12/1975 | Mookherjee et al. | 568/377 |
| 4,272,412 | 7/1981 | Willis et al. | 568/377 |
| 4,626,602 | 12/1986 | Schulte-Elte et al. | 568/822 |
| 4,868,339 | 9/1989 | Christenson et al. | 568/376 |
| 5,017,711 | 5/1991 | Chapuis et al. | 549/332 |

FOREIGN PATENT DOCUMENTS

| | | | |
|---|---|---|---|
| 0075237 | 3/1983 | European Pat. Off. | 512/22 |
| 0121828 | 10/1984 | European Pat. Off. | 512/22 |
| 0210391 | 2/1987 | European Pat. Off. | 512/22 |
| 0374509 | 6/1990 | European Pat. Off. | 512/22 |
| 2455761 | 6/1976 | Fed. Rep. of Germany | 512/22 |
| 2404616 | 4/1979 | France | 512/22 |
| 61-243041 | 10/1986 | Japan | 512/22 |
| 62-051637 | 3/1987 | Japan | 512/22 |

OTHER PUBLICATIONS

Chemical Abstracts registry Handbook [1965-1971] [R1] 1R-2024R, 1974, American Chemical Society, Columbus, Ohio.

B. Maurer, et al., "New Irone-Related Constituents from the Essential Oil of *Iris germanica* L.", 72 Helvetica Chimica Acta, 6, pp. 1400-1415 (Sep. 20, 1989).

Primary Examiner—James H. Reamer
Attorney, Agent, or Firm—Pennie & Edmonds

[57] ABSTRACT

Novel compounds of formula

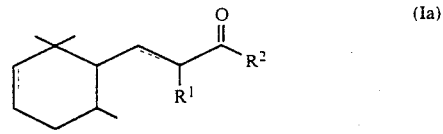

wherein the dotted lines indicate the location of a single or double bond, symbol $R^1$ stands for a hydrogen atom or a methyl radical, symbol $R^2$ represents a linear or branched, saturated or unsaturated, $C_1$ to $C_4$ alkyl radical, provided that $R^1$ is not hydrogen when $R^2$ represents a methyl or n-propyl radical and the ring is saturated. Compounds (Ia) are useful as perfuming ingredients.

A process for their preparation is disclosed.

6 Claims, No Drawings

CYCLIC KETONES AND THEIR USE AS PERFUMING INGREDIENTS

BRIEF SUMMARY OF THE INVENTION

The present invention relates to the art of perfumery and to the synthesis of novel fragrant compounds, in particular of new cyclic ketones which are useful for the preparation of perfuming compositions and perfumed articles.

One object of the present invention is to provide novel compounds of formula

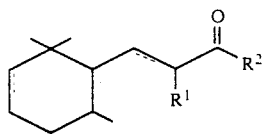

(Ia)

wherein the dotted lines indicate the location of a single or double bond, symbol $R^1$ stands for a hydrogen atom or a methyl radical, symbol $R^2$ represents a linear or branched, saturated or unsaturated, $C_1$ to $C_4$ alkyl radical, with the proviso that $R^1$ cannot be hydrogen when $R^2$ represents a methyl or n-propyl radical and the ring is saturated, as well as specific isomers thereof.

Compounds (Ia) and their isomers are useful perfuming ingredients and can be used in the preparation of perfuming compositions and perfumed articles of varied nature.

Another object of the invention is thus to provide a method to confer, improve, enhance or modify the odor properties of a perfuming composition or a perfumed article, which method comprises adding to said composition or article a fragrance effective amount of a compound of formula

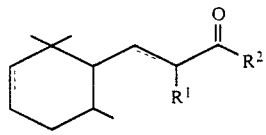

(Ia)

wherein the dotted lines indicate the location of a single or double bond, symbol $R^1$ designates a hydrogen atom or a methyl radical and symbol $R^2$ stands for a linear or branched, saturated or unsaturated, $C_1$ to $C_4$ alkyl radical.

The invention further provides perfuming compositions and perfumed articles resulting from the method described above.

Yet another object of the invention is a process for the preparation of a compound of formula

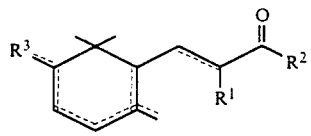

(I)

wherein the dotted lines indicate the location of a single or double bond, symbol $R^1$ designates a hydrogen atom or a methyl radical, symbol $R^2$ represents a linear or branched, saturated or unsaturated, $C_1$ to $C_4$ alkyl radical and symbol $R^3$ stands for a methyl, ethyl or methylene radical, which method comprises the following steps:

a. treating a compound of formula

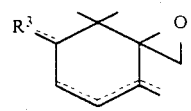

(II)

wherein the dotted lines and symbol $R^3$ are defined as above, with a Lewis type acid to obtain an aldehyde of formula

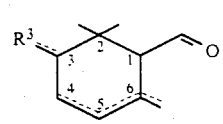

(III)

wherein the dotted lines and symbol $R^3$ have the meaning given above;

b. if necessary, converting, through a conventional isomerization reaction, an aldehyde of formula (III) having an endocyclic double bond in position 5 into its isomer of formula

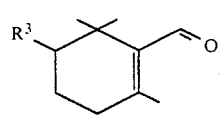

(IIIb)

wherein $R^3$ has the meaning indicated above;

c. converting, by an aldol condensation reaction with an appropriate ketone of formula

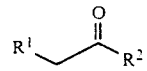

wherein $R^1$ and $R^2$ are defined as in formula (I), the aldehyde obtained according to step a. or b. into a compound of formula (I) having a double bond in the side chain; and d. if necessary, subjecting the latter compound to a conventional hydrogenation or reduction reaction to obtain a compound of formula (I) having a saturated side chain.

The invention further relates to compounds of formula (II) or (III) or (IIIb) which are useful precursors of the compounds of formula (I) and, more particularly (Ia), defined above.

Another process according to the present invention allows the preparation of a compound of formula (III) as defined above and comprises treating with a Lewis type acid a compound of formula (II) defined as above.

BACKGROUND OF THE INVENTION

U.S. Pat. No. 4,626,602 discloses a process which enables the preparation of cyclic ketones of formula

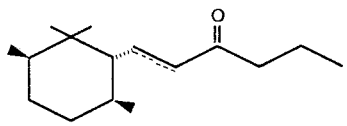

wherein the dotted line indicates the location of a single or double bond. These ketones are cited as useful intermediate products in the preparation of the corresponding saturated alcohol, which is useful in perfumery, and the process described may be illustrated by the following scheme:

SCHEME I

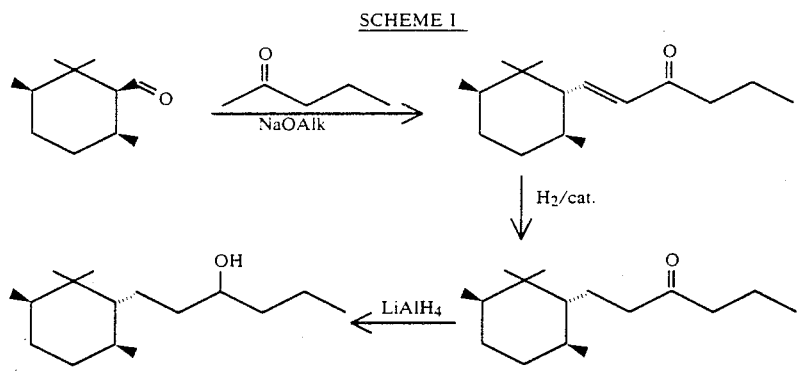

According to the same document, 2,2,3,6-trimethyl-1-cyclohexanecarbaldehyde, used as the starting product in said process, could be obtained from an ester derivative of α-cyclogeranic acid, following a method which may be illustrated as follows:

SCHEME II

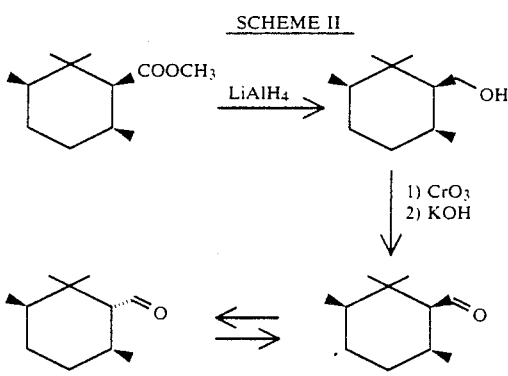

The prime importance of said carbaldehyde as an intermediate product for the preparation of fragrant ketones and alcohols is cited in the above-mentioned U.S. patent.

On the other hand, U.S. patent application Ser. No. 07/450,148, filed on Dec. 13, 1989 and claiming Swiss priority of Dec. 21, 1988, brought another contribution into this field by disclosing a method for the preparation of specific and more advantageous isomeric forms of the above-mentioned carbaldehyde, forms which could not up to then be obtained in a useful yield. The process described in said patent application is represented in the following scheme, wherein the wavy line designates a C—C bond of cis or trans configuration and the two methyl groups in positions 3 and 6 of the ring have a trans configuration:

SCHEME III

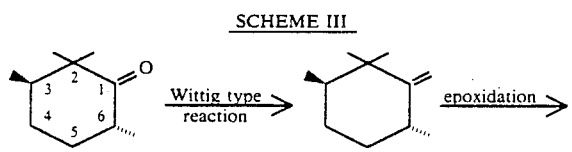

-continued
SCHEME III

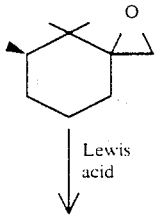

Lewis acid

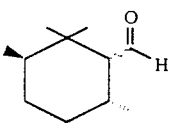

The aim of the two processes illustrated in Schemes I and III and described in the two documents cited was to provide a method enabling the preparation of trans configuration isomers of 1-(2,2,3,6-tetramethyl-1-cyclohexyl)-3-hexanol, isomers which were particularly useful in perfumery, 1-(2,2,3,6-tetramethyl-1-cyclohexyl)-1-hexen-3-one and 1-(2,2,3,6-tetramethyl-1-cyclohexyl)-3-hexanone being just intermediate products in the overall process.

We have now discovered that the principle on which rest these two processes can be successfully applied to the synthesis of new fragrant compounds and that it provides, moreover, a new method for the preparation of α-, β- and γ- irones and ionones, well-known and appreciated compounds in perfumery, as well as of their homologues. Although there have been to this day many reports related to the preparation of these compounds [see, for example, P. Z. Bedoukian, Perfumer and Flavoring Synthetics, Allured Publishing Corporation, 3rd ed. USA (1986)], the synthesis of irones in particular is still very costly, so that efforts are still being made to find simpler and more economic syntheses of said compounds. The present invention brings an advantageous and original solution to this problem and, namely, to the problem of synthesizing particularly useful and specific stereoisomeric forms of these compounds, racemic or optically active. If further provides novel ketones which possess unexpected and surprisingly useful odor properties.

THE INVENTION

As it has been previously cited, it is an object of the present invention to provide a process for the preparation of a compound of formula (I), comprising the steps described above.

This process enables the preparation of novel ketones having useful and unexpected odor properties. It further provides a new and advantageous solution to the problem of synthesizing known odoriferous compounds, prized in perfumery, such as irones and their homologues. Step a. of this process, which is also an object of the present invention, effectively enables the preparation of the precursor aldehydes for such compounds, starting from novel compounds, i.e. epoxides (II) defined above.

Novel epoxides (II) can be prepared according to an original process, starting from ketones of formula

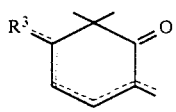
(V)

having a single or double bond in the positions indicated by the dotted lines and wherein symbol $R^3$ has the meaning indicated in formula (I), following a method analogous to that represented in scheme III. Alternatively, they can be prepared according to new methods analogous to those described in the U.S. patent application already cited, the contents of which are here included by reference, which methods resort to the use of Corey-Chaykovsky type reactions. The conditions under which the above-mentioned methods are applied are described in detail, case by case, in the examples of preparation of epoxides (II) presented further on.

As it has been previously mentioned, novel epoxides of formula (II) thus obtained, and, likewise, the aldehydes of formula (III) derived therefrom, are compounds of prime importance in the fragrance industry, in their role as precursors of irones and their analogue compounds, and are also an object of the present invention.

It should be noted that the process according to the invention also allows the preparation of α-, β- or γ-ionones and their homologues, starting from epoxides of formula

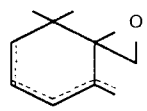

wherein the dotted lines indicate the location of a single or double bond. Several such epoxides are compounds of known structure. Examples of their preparation, as well as of the preparation of the corresponding aldehydes, are described further on.

According to the invention, the epoxides of formula (II) are converted into aldehydes of formula (III) defined above by means of a reaction with a Lewis type acid. Such reactions are analogous to those described in U.S. Pat. No. 5,017,711 and the pertinent teachings there-contained in this regard are here included by reference. The specific conditions of these reactions are described in each case in the respective preparation examples.

If necessary, the aldehydes of formula (I) having an endocyclic double bond in position 5 are converted, by way of conventional isomerisation reactions, into their isomers of formula

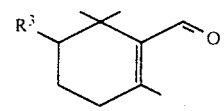
(IIIb)

wherein symbol $R^3$ is defined as in formula (III), which are useful precursors for the preparation of β-irones and their analogues. It goes without saying that, in a similar manner, the aldehydes of formula (IIIb) wherein $R^3$ stands for hydrogen, which are β-ionones precursors, can be obtained from their corresponding position isomers. The specific conditions of the cited isomerisation reactions are described further on.

Aldehydes of formula (III) or (IIIb), excluding 2,2,3,6-tetramethyl-1-cyclohexanecarbaldehyde already disclosed in the cited U.S. Pat. No. 4,626,602, are another object of the present invention.

According to the process of the invention, the aldehydes of formula (III) or (IIIb) are converted, by means of an aldol condensation reaction with an appropriate ketone of formula

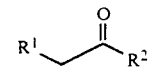

wherein $R^1$ and $R^2$ are defined as in formula (I), into compounds of formula (I) having a double bond in the side chain. If necessary, the latter are then converted into their saturated-chain analogues by way of conventional hydrogenation or reduction reactions.

According to a preferred embodiment of the process of the invention, a compound of formula (Ia) is prepared by using as a starting product a compound of formula

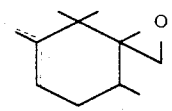
(IIa)

wherein the dotted lines have the same meaning as in formula (Ia).

Other particularly preferred embodiments of the process according to the invention enable the preparation of specific isomers of compounds of formula (I) or (Ia) starting from the appropriate isomers of epoxides of formula (II) or (IIa).

It is thus that a compound essentially in a trans configuration isomeric form of formula

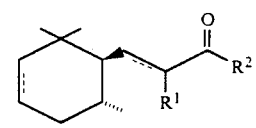
(Ib)

wherein the dotted lines in the ring indicate the location of a double bond, the dotted line in the side chain indicates the location of a single or double bond, symbol $R^1$ stands for an hydrogen atom or a methyl radical and symbol $R^2$ represents a linear or branched, saturated or unsaturated, $C_1$ to $C_4$ alkyl radical, in the form of a racemate or of any one of the optically active enantiomers, is prepared by using, as a starting product, an epoxide essentially in a trans configuration isomeric form of formula

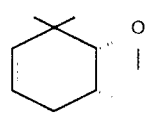 (IIb)

wherein the dotted lines are defined as in formula (Ib), or any one of its optically active enantiomers.

Likewise, a compound essentially in a trans configuration isomeric form of formula

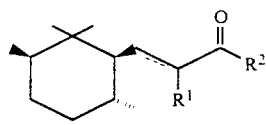 (Ic)

wherein the dotted line indicates the location of a single or double bond and symbols $R^1$ and $R^2$ are defined as in formula (Ib), in the form of a racemate or of any one of the optically active enantiomers, is prepared by using, as a starting product, an epoxide essentially in a trans configuration isomeric form of formula

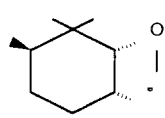 (IIc)

or any one of its optically active enantiomers.

According to the invention, the epoxides of formula (IIa) defined above, which make it possible to prepare aldehydes of formula

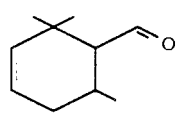 (IIIa)

wherein the dotted lines indicate the location of a double bond, and, more particularly, the racemic or optically active stereoisomers of formula (IIb) or (IIc), or yet of formula

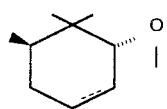 (IId)

wherein the dotted lines indicate the location of a double bond, are preferred starting products, specifically adapted to the preparation of preferred stereoisomers of compounds (I), the odor properties of which are particularly interesting, as becomes obvious from the remarks presented further on.

Scheme III illustrates the manner in which these various stereoisomers of epoxides (II) can be obtained by using, as a starting product, an appropriate stereoisomer of ketone (V). In the same way, racemic mixtures or optically active isomers of the desired epoxides can be prepared from racemic mixtures or, respectively optically active isomers, of the starting ketone, as described in the preparation examples disclosed further on.

According to the process of the invention, the cited preferred epoxides are converted into the corresponding aldehydes. Amongst the latter, the racemic stereoisomers of formula

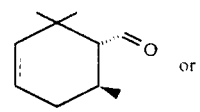 (IIIc)
or

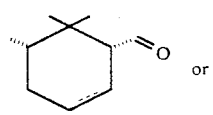 (IIId)
or

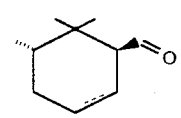 (IIIe)

wherein the dotted lines indicate the location of a double bond, or any one or their optically active enantiomers, are cited as preferred compounds of the invention.

Compounds (I) of the invention can also be prepared according to an alternative process, wherein aldehyde (III) is obtained through a series of reactions such as those illustrated in scheme II. We observed that this process was particularly useful for the preparation of compounds of formula (Ia) possessing a double bond in one of the positions of the ring indicated by the dotted lines, and that it could be advantageously used for the synthesis of trans configuration isomers of formula (Ib). This process, examples of which are presented further on, uses a reduction reaction of a starting ester of formula

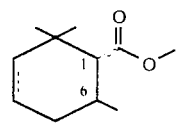 (VI)

wherein the dotted lines have the meaning described above and the wavy line designates a cis or trans configuration C—C bond with regard to the methyl substituent group in position 6, said reduction being carried out by means of an alkali metal aluminohydride and providing an alcohol of formula

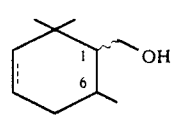 (VII)

wherein the dotted lines and the wavy line are defined as in formula (VI). The reduction is followed by a treatment of said alcohol (VII) with an oxidizing agent to give an aldehyde of formula

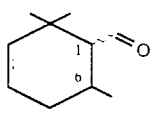

(IIIa)

wherein the dotted lines and the wavy line have the meaning indicated.

The reduction of the ester of formula (VI) can be realized by means of LiAlH4, for example, and, as the oxidizing agent of the alcohol (VII) obtained, one can use for instance pyridinium chlorochromate (PCC) in dichloromethane. The aldehyde of formula (III) which results from the oxidation reaction is then converted into the desired compound (I) through reactions such as those represented in scheme I, i.e., an aldol condensation followed, if necessary, by a hydrogenation.

The specific conditions of these reactions are described in detail in the preparation examples presented further on.

The esters of formula (VI) used as starting products in this process are novel compounds. They can be prepared from a mixture of isomers of methyl geranate, following the reaction scheme represented hereinafter:

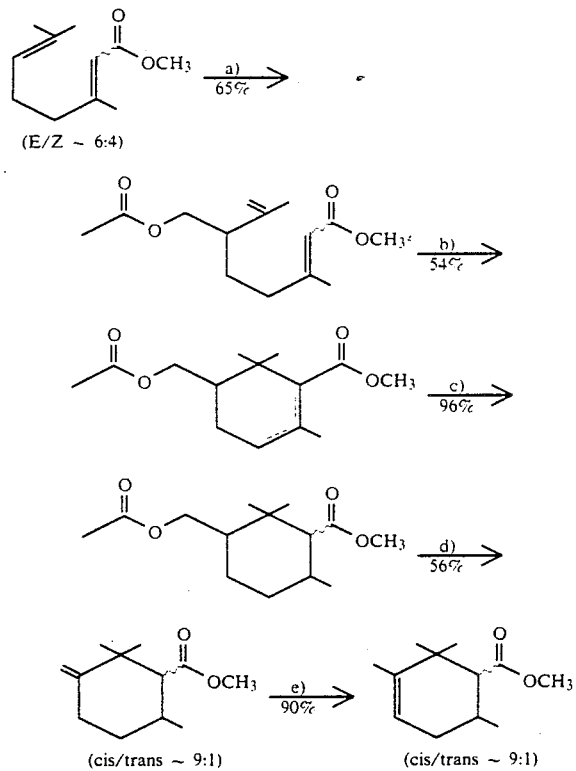

a) CH2O; (CH3CO)2O; BF3.Et2O
b) CH3COOH; SnCl4;
c) H2; PtO2; CH3COOH;
d) 430°; N2;
e) TsOH; toluene As indicated in this scheme, esters (VI) are obtained as a mixture of isomers rich in isomer cis. The isomeric ratio indicated remains substantially the same upon the conversion of these esters into alcohols (VII) and, subsequently, of the latter into aldehydes (IIIa). The aldol condensation of these aldehydes is accompanied by an epimerisation, which is more or less complete, to give the desired ketone in its trans configuration form (Ib).

Amongst the compounds of formula (Ia) according to the invention, there are some of known chemical structure. For example, 1-(2,2,3,6-tetramethyl-1-cyclohexyl)-1-hexen-3-one and 1-(2,2,3,6-tetramethyl-1-cyclohexyl)-3-hexanone were described in U.S. Pat. No. 4,626,602 as intermediate products in the synthesis of 1-(2,2,3,6-tetramethyl-1-cyclohexyl)-3-hexanol. However, we did not find in this patent any mention that these two ketones might be useful odoriferous substances.

In addition, references can be found in the literature of 4-(2,2,3,6-tetramethyl-1-cyclohexyl)-2-butanone and 4-(2,2,3,6-tetramethyl-1-cyclohexyl)-3-buten-2-one. For example, several isomers of the first named are cited by A. Storni in his Doctorate Thesis, ETH, Juris-Verlag, Zürich (1962) in relation to a study of the configuration of γ-irone. On the other hand, the structure of the above-mentioned butenone is disclosed by P. Bächli et al. in Helv. Chim. Acta 34, 1168 (1951). In spite of their efforts, the latter authors did not succeed in identifying the various isomers of the cited enone. None of the works cited mentions any particular fragrant properties of these ketones. As a matter of fact, the reports cited were the result of studies which were part of a comprehensive program aiming at elucidating the correct structure of the irones, a much controversial subject at the time [see, for example, Y. R. Naves et al., Bull. Joc. Chim. France 1953, 112 and references cited therein] and the particular odor properties of their dihydro and tetrahydro derivatives cited above were completely overlooked.

It is, in fact, not surprising that the olfactive properties of these ketones did not call the perfumers' attention at the time, since their structure was very close to that of the irones, ionones and methylionones which formed an already impressive body of well-known and appreciated fragrant products. The latter constituted in fact the prime subjects of research and there was no reason to expect that novel odoriferous compounds with a similar type of structure could still be found, whose olfactive qualities would not merely emulate those of the already known compounds.

Yet, we have now observed that not only do the known ketones of formula (Ia) cited above possess very useful odor properties, quite distinct from those of the prior art compounds of similar structure, but that novel ketones of analogous structure which obey formula (Ia) and are the object of the present invention can be advantageously used for the preparation of perfuming compositions and perfumed products, as a result of the originality and individuality of their olfactive qualities.

Moreover, we have also discovered that amongst the various possible isomers of the present series of compounds of formula (Ia), the cyclanic trans configuration isomers of formula (Ib) defined above possessed olfactive properties which were systematically judged to be superior to those of the corresponding cis isomers. In particular, we have been able to establish that, amongst the compounds of formula (Ia) having a saturated ring, the isomers whose substituents in positions 1, 3 and 6 of the ring possess an equatorial configuration, represented by formula (Ic) defined above, possessed more distinctive and preferred odor characters than their corresponding isomers which had different configurations.

In spite of their very close structure to that of the irones and ionones, and of the slight structure variations from one compound to the next, the compounds of the invention bring into the range of the iris-violet odor notes a rich variety of olfactive tonalities, occasionally combined with remarkable variations in the intensity and tenacity of the odor.

Table I which summarizes the olfactive properties of preferred compounds of the invention, occasionally in various isomeric forms, emphasizes these observations.

TABLE I

| No | Compounds | Olfactive properties |
|---|---|---|
| 1 | 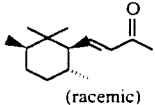 (racemic) | iris-violet note, powdery, balsamic, reminiscent of myrrh, woody, exceptional strength and tenacity |
| 2 | 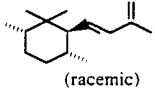 (racemic) | woody note, similar to that above, less irone like, much weaker than 1 |
| 3 | 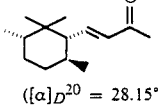 ($[\alpha]_D^{20} = 28.15°$) | iris-irone note with a very warm balsamic-myrrh, woody character. The violet-iris character is more pronounced than in 1 and the odor note is even stronger |
| 4 | 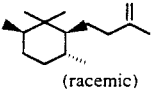 (racemic) | weaker and less iris-type odor than 1 |
| 5 | 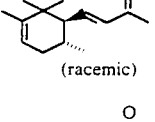 (racemic) | stronger woody character than 1, very natural note, reminiscent of cedar and sandalwood; bottom leather note |
| 6 | 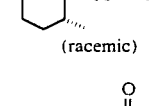 (racemic) | iris-violet note, nice woody character, closer to irone type odor than the others |
| 7 | 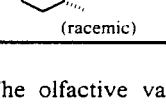 (racemic) | fruity-floral note, apricot, freesia, woody |

The olfactive variety illustrated in this table was observed throughout the other compounds of the invention, the properties of which are described in detail in the preparation examples.

Amongst the compounds of the invention, and in particular those cited in this table, (E)-4-(2,2,c-3,t-6-tetramethyl-r-1-cyclohexyl)-3-buten-2-one (compound 1) is the compound which possesses the olfactive properties best adapted to certain perfumery applications according to the invention. For example, its use in perfuming compositions confers to the latter a powdery and oriental character of great quality, quite apparent even at very weak concentrations of said compound, and which is surprisingly rich and performant, and all the more striking when compared to the performance of irones, ionones and methylionones and, namely, α-irone. The tenacity of its odor note is far superior to that of the notes of the cited prior art compounds, as it is apparent from the results of the comparative essays of substantivity on textiles described further on.

However, other compounds according to the invention can be advantageously used in various applications, depending on the olfactive effect desired, on the nature and aim of the product to be perfumed.

The compounds of the invention can be used in a variety of perfuming compositions, their effect being equally appreciated in both feminine and masculine type compositions, intended for perfumes and Colognes, to which they impart a warm and rich character. In addition they are also quite advantageously used in the perfuming of soaps and other personal care and hygiene products such as bath or shower gels, deodorants, shampoos and hair creams, as well as cosmetic preparations. They are also useful for perfuming household products, or yet, detergents and fabric softeners, a field where (E)-4-(2,2,c-3,t-6-tetramethyl-r-1-cyclohexyl)-3-buten-2-one turns out to be yet a choice product owing to the tenacity of its odor.

The concentrations in which the compounds of formula (Ia-c) may be used to achieve the desired effects can vary in a wide range of values. The man in the art knows by experience that such values are dependent on the particular effect that is desired, as well as on the nature of the products to be perfumed. It is also known that these values are a function of the nature of the other co-ingredients in a given composition, when the compounds of the present invention are used as ingredients in perfuming bases and concentrates, in admixture with other co-ingredients, solvents or current adjuvants.

Proportions of the order of 1 to 10%, or even 20% by weight, relative to the weight of the composition, may be cited by way of example, when the compounds are used in the preparation of perfuming bases and concentrates. Considerably lower concentration values may be used when perfuming articles such as soaps and cosmetics or detergents.

According to the invention, a compound (Ia-c) will be either directly incorporated in the article to be perfumed or, more generally, it will be used in admixture with other perfuming ingredients of current use in perfumery. Specific citation of said co-ingredients is here quite superfluous, as there are many prior art examples and the man in the art is quite able to chose those more adapted to the odor effect to be achieved. In this context, the reference book of S. Arctander, Perfume and Flavor Chemicals, Montclair, N.J., U.S.A. (1969) can be cited.

The perfuming compositions and perfumed articles containing as an active ingredient a compound of formula (Ia) to (Ic) according to the invention are another object of the latter. Preferred such compositions and articles result from the use of the cited preferred compounds of the invention and particularly preferred are those resulting from the use of (E)-4-(2,2,c-3,t-6-tetramethyl-r-1-cyclohexyl)-3-buten-2-one, racemic or optically active, as a perfuming ingredient.

The invention will now be disclosed in greater detail by way of the preparation examples described hereinafter, wherein the temperatures are indicated in degrees centigrade and the abbreviations have the usual meaning in the art.

The invention will also be illustrated by way of examples of perfumery applications.

EXAMPLE 1

Preparation of Epoxides of Formula (II)

General Method

The method used for the preparation of these epoxides can be represented by the following scheme:

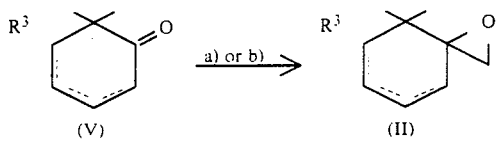

a) $(CH_3)_3S^-CH_3SO_4^-$, NaH (ou NaOH), DMSO
b) $(CH_3)_3S^-X^-(X=Cl,I)$, NaH (NaOH), DMSO

As it has been described in the European patent application published under N°. 0 374 509 on Jun. 26, 1990, the dimethylsulfonium methylide used as a reagent in the Corey-Chaykovsky type reaction, is formed in situ in the reaction medium by reacting either dimethylsulfide and dimethylsulfate, or trimethylsufonium halide, with sodium hydride or hydroxide in dimethylsulfoxide (DMSO), according to the following method.

A three-neck vessel equipped with an appropriate condenser, a dropping funnel and a magnetic stirrer, kept under inert atmosphere, was charged with dimethylsulfate and dimethylsulfide was slowly added thereto. The exothermic reaction was cooled down with an ice bath so as to maintain a reflux of dimethylsulfide. Once this reflux had almost stopped, DMSO was added to the reaction in order to dissolve the salt formed. The cooling bath was removed for 10 minutes during which stirring was continued, and the mixture was then cooled to 20° once again.

At this temperature, 75% sodium hydride in mineral oil (or sodium hydroxide in pearls). After stirring for about 30 min. a DMSO solution of the appropriate ketone was added to the mixture at a temperature varying between 0° and 6°, depending on the case. The reaction mixture was then kept under stirring at room temperature, over a period of time sufficient to garanty complete consumption of the starting ketone.

Ethyl acetate was then added, followed by slow addition of water. The aqueous phase was extracted successively with petroleum ether (30°-50°), ethyl acetate and again petroleum ether (30°-50°). The organic layers were combined and washed to neutrality with an appropriate solution, followed by water. After drying over $Na_2SO_4$ or $MgSO_4$, the obtained product was filtered and evaporated to yield the raw product. Bulb-to-bulb distillation of the latter afforded the desired compound in a pure state.

When trimethylsulfonium halide was used as reagent, instead of dimethylsulfide and dimethylsulfate, the sodium hydride (or NaOH) was added to a solution of said reagent in DMSO, in a reactor of the type already mentioned, and the appropriate ketone was added in DMSO solution. The procedure was then followed as previously described.

Following this general method, the epoxides described hereinafter were prepared.

a. Trans-4,4,8-trimethyl-1-oxaspiro[2.5]octane and cis-4,4,8-trimethyl-1-oxaspiro[2.5]octane These compounds were prepared in a 3-neck vessel equipped with a dry-ice condenser, under argon. 30 G (239 mmol) of $(CH_3)_2SO_4$, 16 g (257 mmol) of $(CH_3)_2S$, 50 ml of DMSO and 41 g (1026 mmol) of NaOH were used. A solution of 2,2,6-trimethylcyclohexanone (24 g, 171 mmol) in 25 ml of DMSO was added at 6°. The mixture was stirred for 6 h. Ethyl acetate (100 ml) was added and then, at 0°, 300 ml of water. Extraction was carried out with $2\times 100$ ml of petroleum ether and 100 ml of ethyl acetate. The combined organic layers were washed with $2\times 100$ ml of a solution saturated with NaCl and 100 ml of water. After drying and filtering, 23.6 g of raw oil were distilled to give 21.4 g of a 94% pure mixture containing 68% of trans isomer and 32% of cis-isomer of the above-mentioned oxaspiro compound.

B.p.: $100°/6\times 10^2$ Pa; yield 76%.
IR: 2980, 1480, 1395 $cm^{-1}$.
cis-isomer
NMR($^1$H, 360 MHz): 0.70(d, J=7 Hz, 3H); 1.08(s, 3H); 1.20-2.20(m, 7H); 2.63(s, 2H) δ ppm.
NMR($^{13}$C): 14.9(q); 22.2(t); 24.4(q); 24.5(q); 30.2(d); 33.2(t); 34.4(s); 38.3(t); 45.9(t); 64.3(s) δ ppm.
MS: 154(M$^+$, 9), 139(45), 109(100), 81(57), 69(52), 67(78), 55(53), 41(69).
trans-isomer
NMR($^1$H, 360 MHz): 0.72(d, J=7 Hz, 3H); 0.77(s, 3H); 1.07(s, 3H); 1.20-2.20(m, 7H); 2.65(AB, J=5 Hz, Δv=32 Hz, 2H) δ ppm.
NMR($^{13}$C): 15.0(q); 21.7(t); 22.5(q); 25.7(q); 31.6(d); 34.7(s); 35.2(t); 40.5(t); 45.9(t); 65.4(s) δ ppm.
MS: 154(M$^+$, 9), 139(42), 109(100), 81(52), 69(58), 67(76), 55(55), 41(69).

b. 4,8,8-trimethyl-1-oxaspiro[2.5]oct-4-ene

Prepared under the conditions described in a., starting from 25.0 g (181 mmol) of 2,6,6-trimethyl-2-cyclohexen-1-one, 31.9 g (253 mmol) of $(CH_3)_2SO_4$, 17.0 g (274 mmol) of $(CH_3)_2S$ and 43.0 g (1086 mmol) of NaOH in 60 ml of DMSO. 22.09 G of the desired product, 91% pure, were obtained.

B. p.: $100°/6\times 10^2$ Pa; yield 73%.
IR: 2970, 1680, 1450 $cm^{-1}$.
NMR($^1$H, 360 MHz): 0.88(s, 3H); 0.92(s, 3H); 1.53(s, 3H); 2.87(AB, J=4 Hz, Δv=15 Hz, 2H); 5.77(broad s, 1H) δ ppm.
NMR($^{13}$C): 17.1(q); 22.6(q); 22.8(t); 24.3(q); 32.15(s); 35.5(t); 48.1(t); 62.7(s); 129.2(d); 129.2(s) δ ppm.
MS: 152(M$^+$, 12), 137(42), 124(100), 107(77), 91(55), 79(55), 41(42).

c. 4,4-dimethyl-8-methylene-1-oxaspiro[2.5]octane

Prepared according to the previously described general method, starting from 4.5 g (25.0 mmol) of 75% pure 2,2-dimethyl-6-methylene-1-cyclohexanone in 5 ml of DMSO, added to a solution of 4.8 g (42.4 mmol) of trimethylsulfonium chloride and 13.0 g (326 mmol) of sodium hydroxide in 30 ml of DMSO. The mixture was stirred for 3 h and 50 ml of ethyl acetate were added, followed by 100 ml of water. The aqueous phase was extracted with $3\times 50$ ml of ethyl acetate and the organic layer was washed with a 10% solution of HCl and with water, and dried over $MgSO_4$. Distillation of the product gave 1.25 g of the desired epoxide (94% pure, yield 32%).

IR: 3060, 2950, 1660, 1460 $cm^{-1}$.
NMR ($^1$H, 360 MHz): 0.83(s, 3H); 0.94(s, 3H); 2.45(d, J=5 Hz, 1H); 2.93(d, J=5 Hz, 1H); 4.75(broad s, 1H); 4.90(broad s, 1H) δ ppm.

NMR($^{13}$C): 22.65(t); 22.75(q); 24.3(q); 34.79(s); 34.92(t); 39.6(t); 52.5(t); 65.1(s); 107.49(t); 146.76(s) δ ppm.

MS: 152(M$^+$, 8), 137(100), 123(33), 109(89), 96(45), 91(50), 81(89), 79(70), 69(63), 67(66), 41(80).

d. 4,4,t-5,r-8-tetramethyl-1-oxaspiro[2.5]octane

Prepared according to the general method described, starting from 2,2,3,6-tetramethyl-1-cyclohexanone (mixture trans/cis: 85/15%) under the conditions described in published European patent application No. 0 374 509. The analytical data for this epoxide are described therein. When using as starting product (+)-(3S,6S)-2,2,3,6-tetramethyl-1-cyclohexanone ($[\alpha]^{20}_D = +52.2°$) or, respectively (−)-(3R,6R)-2,2,3,6-tetramethyl-1-cyclohexanone ($[\alpha]^{20}_D = -50.7°$), there were obtained the optically active isomers of the above-mentioned epoxide, i.e., (+)-(3S,5S,8S)-4,4,5,8-tetramethyl-1-oxaspiro[2.5]octane ($[\alpha]^{20}_D = +36.0°$) or, respectively (−)-(3R,5R,8R)-4,4,5,8-tetramethyl-1-oxaspiro[2.5]octane ($[\alpha]^{20}_D = -35.1°$). The analytical data of these compounds are also described in said European patent application.

e. (3RS,7SR)-4,7,8,8-tetramethyl-1-oxaspiro[2.5]oct-4-ene

Prepared according to the described general method, starting from 40 g (263 mmol) of 2,5,6,6-tetramethyl-2-cyclohexen-1-one and 1.6 equivalent of (CH$_3$)$_2$S/(CH$_3$)$_2$SO$_4$/NaH in 40 ml DMSO. After 15 h of reaction, 100 ml of ethyl acetate were added, followed by 100 ml of water, added dropwise. The aqueous phase was washed with 100 ml of petroleum ether (30°–50°) and 100 ml of ethyl acetate. The combined organic phases were washed with 2×100 ml of water, dried over Na$_2$SO$_4$ and evaporated. After distillation of the raw product (42.3 g) which consisted of a mixture containing, other than the desired compound, 9% of the starting ketone, the above-mentioned epoxide was obtained.

IR: 3020, 2900, 1440, 1360 cm$^{-1}$.

NMR($^1$H, 360 MHz): 0.78(s, 3H); 0.86(s, 3H); 0.91(d, J=7 Hz, 3H); 1.50(broad s, 3H); 2.77(AB, J=4 Hz, Δν=50 Hz, 2H); 5.66(broad s, 1H) δ ppm.

MS: 166(M$^+$, 10), 151(35), 137(30), 124(100), 121(50), 109(32), 105(40), 95(40), 91(35), 79(35), 41(55).

Using (+)-(5S)-2,5,6,6-tetramethyl-2-cyclohexen-1-one ($[\alpha]^{20}_D = +79.5°$) as starting product and following the same method, we obtained (+)-(3R,7S)-4,7,8,8-tetramethyl-1-oxaspiro[2.5]oct-4-ene ($[\alpha]^{20}_D = +53°$).

f. (+)-(3R,5S)-4,4,5-trimethyl-8-methylene-1-oxaspiro[2.5]octane

Prepared from 10.4 g (0.092 mol) of trimethylsulfonium chloride, 10 ml of DMSO and 13.15 g (0.33 mol) of NaOH in dragets (added all at once). After cooling with an ice bath, 10 g (0.066 mol) of (+)-(3S)-2,2,3-trimethyl-6-methylene-1-cyclohexanone ($[\alpha]^{20}_D = +6.7°$, 5% CHCl$_3$) in solution in 10 ml of DMSO were added dropwise, under vigorous stirring, while maintaining the temperature at 6° or lower. After room temperature stirring overnight, the mixture was cooled with an ice bath and hydrolysed with water, without letting the temperature go above 20°. After the usual treatment, 8.6 g of raw product were obtained. The latter was distilled on residues and, then, finely on a Fischer column. 1.6 G of 75% pure epoxide were obtained.

$[\alpha]^{20}_D = +22.8°$, c=5.2% CHCl$_3$.

B.p.: 58°/0.9×10$^2$ Pa; yield 15%.

IR: 3060, 2990, 2950, 1660, 1460 cm$^{-1}$.

NMR($^1$H, 360 MHz): 0.77(s, 3H); 0.83(s, 3H); 0.90(d, J=7 Hz, 3H); 2.33(d, J=7 Hz, 1H); 2.90(d, J=7 Hz, 1H); 4.69(broad s, 1H); 4.92(broad s, 1H) δ ppm.

NMR($^{13}$C): 15.6(q); 16.7(q); 21.35(q); 31.1(t); 34.0(t); 37.85(s); 41.36(d); 52.86(t); 65.32(s); 106.4(t); 145.56(s) δ ppm.

MS: 166(M$^+$, 9), 151(50), 137(21), 123(33), 109(60), 95(100), 81(68), 67(38), 55(40), 41(17).

g. (+)-(3R,7S)-7-ethyl-4,8,8-trimethyl-1-oxaspiro[2.5]oct-4-ene

Prepared according to the method described, in a vessel equipped with a CO$_2$ condenser and kept under N$_2$, starting from 6.8 g (0.054 mmol) of (CH$_3$)$_2$SO$_4$, 3.3 g of (CH$_3$)$_2$S, 6 ml of THF (tetrahydrofuran), 8 ml of DMSO and 1.7 g (0.054 mol) of 75% NaH in mineral oil. (+)-(5S)-5-Ethyl-2,6,6-trimethyl-2-cyclohexen-1-one (6.6 g, 0.033 mol, $[\alpha]^{20}_D = +82.4°$) in 2 ml of DMSO was added at ~6°. The mixture was stirred over the week-end and then 21 ml of ethyl acetate were added, followed by 21 ml of water added dropwise. After the usual treatment and distillation on residues, a mixture containing 54% of the desired product was obtained. The desired epoxide was separated from the mixture by further distillation.

$[\alpha]^{20}_D = +54°$.

IR: 2975, 1670, 1460, 1380 cm$^{-1}$.

NMR($^1$H, 360 MHz): 0.80(s, 3H); 0.87(s, 3H); 0.89(t, J~7 Hz, 3H); 1.51(d, J~2 Hz, 3H); 2.77(AB, J=5 Hz, Δν=51 Hz, 2H); 5.69(broad s, 1H) δ ppm.

MS: 180(M$^+$, 5), 165(23), 151(30), 137(22), 133(10), 124(100), 115(2), 105(31), 91(23), 84(7), 79(18), 73(5), 69(15), 59(8), 55(18), 41(55).

EXAMPLE 2

Preparation of Esters of Formula (VI)

a. Methyl 2,2,6-trimethyl-3-methylene-1-cyclohexanecarboxylate

A 3-neck vessel equipped with a condenser, a thermometer and a dropping funnel, kept under N$_2$, was charged with 156 g (0.614 mol) of methyl 6-(acetoxymethyl)-3,7-dimethyl-2,7-octadienoate (trans/cis mixture) [obtained from methyl geraniate by means of a Prins-Blomquist type reaction; see A. T. Blomquist et al., J. Org. Chem. 33, 1156 (1968)] and 750 ml of acetic acid, to which were added, rather quickly, 30 ml of SnCl$_4$. The reaction was slightly exothermic. The mixture was stirred for 15 h at room temperature. It was then poured over saturated NaCl, extracted with ether and washed 5 times with a NaCl solution and once with a NaHCO$_3$ solution. The reaction product was dried over Na$_2$SO$_4$, filtered, concentrated in the rotavapor and distilled on residues. 84 G of a mixture of undetermined isomers of methyl 2-(acetoxymethyl)-2,6,6-trimethyl-1-cyclohexen-1-carboxylate were then obtained. This mixture was used as such in the following synthesis.

B.p.: 95°–105°/6 Pa; yield 54%.

70 G (0.28 mol) of the above-mentioned mixture, in solution in 500 ml of acetic acid, were hydrogenated at atmospheric pressure and room temperature in the presence of 0.3 g of PtO$_2$. After one night, about 7 l of H$_2$ (0.28 mol) had been consumed. The reaction product was filtered, concentrated and distilled on residues to yield 67.7 g of a mixture of undetermined isomers of methyl-3-(acetoxymethyl)-2,2,6-trimethyl-1-cyclohexanecarboxylate. This mixture was used as such in the following synthesis.

B.p.: 79°-88°/6 Pa; yield 96%.

66 G (0.25 mol) of the latter described mixture of isomers were passed over 30 h through a 5 m pyrex column heated at 430°, carried by a small nitrogen flow. The pyrolisate was then distilled over residues to yield 46.1 g of a brown oil (B.p.: 58°-66°/5×10 Pa, 65% pure). Fractionating of this raw product provided 28.3 g of methyl 2,2,6-trimethyl-3-methylene-1-cyclohexanecarboxylate (2 isomers, cis/trans ~ 9:1) in the form of a colorless oil.

B.p.: 42°-43°/16×10² Pa.
IR: 3030, 2950, 1740, 1640, 1440, 1130, 890 cm⁻¹.
NMR($^1$H, 360 MHz): 0.89(d, J=7.2 Hz, 3H); 1.09(s, 3H); 1.17(s, 3H); 1.53(m, 1H); 1.74(m, 1H); 2.14(m, 1H); 2.23-2.43(m, 3H); 3.60(s, 3H); 4.66(s, 1H); 4.78(s, 1H) δ ppm.
MS: 196($M^+$, 1), 164(18), 149(3), 136(23), 121(88), 107(28), 93(35), 81(42), 67(37), 59(26), 55(51), 41(100).

b. Methyl 2,2,3,6-tetramethyl-3-cyclohexen-1-carboxylate

13 G (0.066 mol) of methyl 2,2,6-trimethyl-3-methylene-1-cyclohexanecarboxylate obtained according to a., in solution in 130 ml of toluene, were heated to reflux for 2 h, in the presence of 0.5 g of paratoluenesulfonic acid and under nitrogen. The reaction mixture was washed to neutrality with, successively, a $NaHCO_3$ solution and a NaCl solution, dried over $Na_2SO_4$, concentrated and distilled on residues. 11.7 G of the desired ester (2 isomers, cis/trans ~ 9:1) were obtained in the form of a colorless oil.

B.p.: 40°-43°/1×10 Pa; yield 90%.
IR: 2950, 1740, 1440, 1120 cm⁻¹.
NMR($^1$H, 360 MHz): 0.94(d, J=7.2 Hz, 3H); 1.02(s, 3H); 1.14(s, 3H); 1.66(broad s, 3H); 1.90-2.20(m, 3H); 2.42(d, J=3.6 Hz, 1H); 3.63(s, 3H); 5.4(broad s, 1H) δ ppm.
MS: 196($M^+$, 6), 164(27), 149(4), 136(23), 121(100), 107(13), 96(18), 81(19), 67(10), 41(10).
Odor: fruity, saffran.

EXAMPLE 3

Preparation of Alcohols of Formula (VII)

These alcohols were prepared starting from the esters described in Example 2.

a. 2,2,6-trimethyl-3-methylene-1-cyclohexanemethanol

A 3-neck vessel equipped with a thermometer, a condenser and a dropping funnel, maintained under $N_2$, was charged with 1.5 g (0.04 mol) of $LiAlH_4$ in suspension in 40 ml of sulfuric ether (dry) and a solution of the ester prepared according to example 2a. (8.0 g, 0.04 mol) in 40 ml of sulfuric ether (dry) was added thereto dropwise, while keeping the reaction at reflux. The reaction mixture was kept under stirring for 1 h further, at room temperature, and then cooled down to 0° (icy bath). At this temperature, 1.5 ml of $H_2O$, followed by 1.5 ml of NaOH (15%) and again 4.5 ml of $H_2O$, were carefully added. After ½ h of stirring, the mixture was filtered on sintered glass, well washed with ether, concentrated and bulb-to-bulb distilled. 6.45 G of the desired alcohol were obtained (2 isomers, cis/trans ~ 9:1) in the form of a colorless oil.

B.p.: 150°/3×10² Pa; yield 94%.
IR: 3400, 3120, 2950, 1660, 1460, 1010, 900 cm⁻¹.
NMR($^1$H, 360 MHz, $D_2O$): 1.03(d, J=7.2 Hz, 3H); 1.18(s, 3H); 1.25(s, 3H); 1.25(m, 1H); 1.31(m, 1H); 1.60(m, 1H); 2.21(m, 2H); 2.40(m, 1H); 3.59(dd, $J_1$=3.6, $J_2$=10.8 Hz, 1H); 3.76(dd, $J_1$=2.5 Hz, $J_2$=10.8 Hz, 1H); 4.75(broad s, 1H); 4.76(broad s, 1H) δ ppm.
NMR($^{13}$C): 155.9(s); 107.3(t); 60.9(t); 54.4(d); 39.7(s); 32.9(t); 32.6(t); 30.1(d); 28.5(q); 26.6(q); 19.7(q) δ ppm.
MS: 168($M^+$, 3), 153(9), 135(80), 121(28), 107(100), 95(75), 84(96), 67(68), 55(49), 41(23).

b. 2,2,3,6-tetramethyl-3-cyclohexene-1-methanol

Prepared according to the method described under a., using 1.9 g (0.05 mol) of $LiAlH_4$ in suspension in 60 ml of sulfuric ether, 10.0 g (0.05 mol) of the ester prepared as in example 2b. and 40 ml of ether. The reaction mixture was treated successively with 1.9 ml of water, 1.9 ml of NaOH and 5.7 ml of water. 8.4 G of a mixture containing 90% of cis isomer and 10% of trans isomer of the above-mentioned methanol (colorless oil).

B.p.: 45°/5 Pa; yield 97%.

The major isomer cis desired was purified by gas phase chromatography. Its analytical data were as follows:

IR: 3360, 3000, 1460, 1060, 820 cm⁻¹.
NMR($^1$H, 360 MHz): 1.05(d, J=7.2 Hz, 3H); 1.14(s, 6H); 1.34(m, 1H); 1.66(broad s, 3H); 1.72(m, 1H); 1.98(m, 1H); 2.0(m, 1H); 3.73(m, 2H); 5.32(m, 1H) δ ppm.
MS: 168($M^+$, 12), 153(9), 146(3), 135(89), 119(41), 107(100), 95(68), 91(48), 84(40), 81(65), 67(33), 55(27), 43(20).

EXAMPLE 4

Preparation of Aldehydes of Formula (III) from Epoxides (II)

General Method

This general method may be illustrated by the following scheme:

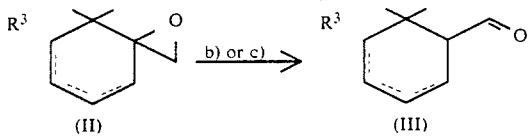

b) $MgI_2$, toluene
c) $SnCl_4$ cat./toluene, 0°

The conversion of epoxide (II) into aldehyde (III) by means of $MgI_2$ in toluene enables a "one-pot" synthesis of cyclic ketones of formula (I) possessing a saturated ring, without need to remove aldehyde (III) from the reaction mixture. $MgI_2$ was prepared in situ, under inert atmosphere, starting from iodine and magnesium in tetrahydrofuran (THF). The latter was then evaporated under reduced pressure and dry toluene was then added and brought to reflux to dissolve the magnesium iodide. After letting it rest for one night at 25°, the mixture was brought to reflux and the appropriate epoxide added thereto. Reflux was maintained under stirring for 30-40 min. The thus formed aldehyde was then either separated after epimerization of the mixture by means of $NaOCH_3$ in methanol, or directly used in the preparation of the corresponding ketone as described in example 6a.

When epoxide (II) was converted into aldehyde (III) by means of SnCl₄ in toluene, we proceeded as follows.

In a reactor under nitrogen, kept at 0°, SnCl₄ was added to a solution of the appropriate epoxide in toluene. After a few minutes of stirring, the reaction mixture was neutralised with an adequate solution and water was added. The aqueous phase was extracted with petroleum ether (30°–50°) and the organic phase was washed with water. The product was dried on Na₂SO₄ and concentrated. The raw material was purified by means of the usual techniques.

In addition, aldehydes of formula (IIIb) were prepared by isomerisation of their α-configuration isomers, under the conditions described further on case by case.

The following aldehydes were prepared:

a. Trans-2,2,6-trimethyl-1-cyclohexanecarbaldehyde and cis-2,2,6-trimethyl-1-cyclohexanecarbaldehyde 20 G (129.9 mmol) of the epoxide prepared as in example 1a. (cis/trans mixture ~68:32) were reacted with magnesium iodide [prepared with 517 mg (21.5 mmol) of Mg and 5.09 g (20 mmol) of I₂ in 20 ml of THF] dissolved in 30 ml of toluene. After bulb-to-bulb distillation (100°/6×10² Pa), 18.74 g (yield 86%) of a 92% pure mixture, containing the two isomers of the desired aldehyde in a ratio cis/trans=43:57, was obtained. This mixture was enriched in trans isomer by epimerisation in 40 ml of methanol, by means of 3 g of a 30% solution of NaOCH₃ in methanol. After reacting for 18 h, 15.6 g (yield 74%) of a 95% pure mixture, containing 95% of trans-2,2,6-trimethyl-1-cyclohexanecarbaldehyde and 5% of cis-2,2,6-trimethyl-1-cyclohexanecarbaldehyde, were obtained.

Trans-2,2,6-trimethyl-1-cyclohexanecarbaldehyde

IR: 2960, 1715, 1455 cm⁻¹.
NMR(¹H, 360 MHz): 0.81(d, J=7 Hz, 3H); 0.97(s, 3H); 1.01(s, 3H); 1.10–2.00(m, 8H); 9.63(d, J=6 Hz, 1H) δ ppm.
MS: 154(M⁺, 23), 139(20), 121(32), 111(26), 83(47), 69(100), 55(54), 41(57).

Cis-2,2,6-trimethyl-1-cyclohexanecarbaldehyde

IR: 2970, 1715, 1440 cm⁻¹.
NMR(¹H, 360 MHz): 0.92(d, J=7 Hz, 3H); 0.93(s, 3H); 1.03(s, 3H); 1.30–2.05(m, 8H); 9.60(d, J=7 Hz, 1H) δ ppm.
MS: 154(M⁺, 17), 139(16), 121(26), 111(24), 95(30), 85(63), 69(100), 55(68), 41(80).

b. 2,2,c-3,t-6-tetramethyl-r-1-cyclohexanecarbaldehyde and
2,2,t-3-c-6-tetramethyl-r-1-cyclohexanecarbaldehyde The preparation of these two aldehydes, starting from the epoxide obtained according to example 1d., was described in published European patent application No. 0 374 509. The respective analytical data are also described therein.

Odor: woody, spicy, patchouli.

An optically active enantiomer of 2,2,c-3,t-6-tetramethyl-r-1-cyclohexanecarbaldehyde, i.e., (+)-(1R,3S,6S)-2,2,3,6-tetramethyl-1-cyclohexanecarbaldehyde [containing 10% of its (1S,3S,6S) diastereomer], was prepared in a similar way starting from (+)-(3S,5S, 8S)-4,4,5,8-tetramethyl-1-oxaspiro[2.5]octane described in example 1d.

The above-mentioned optically active aldehyde was characterized by $[\alpha]^{20}_D = +7.4°$, c=2.5% CHCl₃.

c. 2,6,6-trimethyl-2-cyclohexene-1-carbaldehyde

Prepared by reacting 0.1 ml (0.85 mmol) of SnCl₄ with a solution of 6.6 g (43.42 mmol, 95% pure) of the epoxide obtained as in example 1b, in 66 ml of toluene. After 20 min of stirring, a few drops of a saturated solution of NaHCO₃ were added, then 20 ml of water. The aqueous phase was extracted with 3×20 ml of toluene and the organic phase was washed with 2×30 ml of water. After drying over MgSO₄, evaporation and bulb-to-bulb distillation, 4.88 g (94% pure) of the above-mentioned carbaldehyde, or α-cyclocitral, were obtained.

B.p.: 100°/6×10² Pa; yield 73%.
IR: 2980, 1720, 1680, 1450 cm⁻¹.
NMR(¹H, 60 MHz): 0.87(s, 3H); 0.96(s, 3H); 1.62(broad s, 3H); 5.75(m, 1H); 9.50(d, J=5 Hz, 1H) δ ppm.
MS: 152(M⁺, 5), 123(56), 94(45), 81(100), 67(30).

d. 2,6,6,-trimethyl-1-cyclohexene-1-carbaldehyde

This β-isomer of the aldehyde prepared in c. was obtained by isomerisation of 4.4 g (28.95 mmol) of the latter by means of 1 ml of a 30% solution of NaOCH₃ in methanol (~5.6 mmol), at 20°, during 3 h. The methanol was evaporated and replaced by ethyl acetate. The organic phase was washed with 10 ml of a 10% aqueous solution of HCl, followed by 2×20 ml of water. The product was dried over MgSO₄, evaporated and bulb-to-bulb distilled. 4.25 G of the above-mentioned carbaldehyde, or β-cyclocitral, were obtained (94% pure, yield 73%).

IR: 2980, 1720, 1675, 1615, 1455 cm⁻¹.
NMR(¹H, 60 MHz): 1.20(s, 6H); 2.10(s, 3H); 10.12(s, 1H) δ ppm.
MS: 152(M⁺, 80), 137(100), 123(85), 109(92), 95(46), 81(82), 67(85).

e. 2,2-dimethyl-6-methylene-1-cyclohexanecarbaldehyde

Obtained by reacting 1.1 g (6.8 mmol, 94% pure) of the epoxide prepared according to example 1c., in 10 ml of toluene, with 40 μl (0.34 mmol) of SnCl₄, in 10 min. After the usual treatment, 0.84 g of raw product were obtained, 96.5% of which were converted into the pure desired aldehyde, or γ-cyclocitral, by bulb-to-bulb distillation.

B.p.: 100°/6×10² Pa; yield 78%.
IR: 3100, 2960, 2740, 1725, 1650, 1460 cm⁻¹.
NMR(¹H, 360 MHz): 0.95(s, 3H); 1.07(s, 3H); 2.20(m, 2H); 2.68(d, J=4 Hz, 1H); 4.70(s, 1H); 4.95(s, 1H); 9.84(d, J=4 Hz, 1H) δ ppm.
NMR(¹³C): 22.85(t); 26.0(q); 28.15(q); 33.4(t); 34.95(s); 37.58(t); 66.64(d); 112.4(t); 143.6(s); 203.08(d) δ ppm.
MS: 152(M⁺, 7), 137(24), 123(50), 109(90), 95(43), 94(43), 81(100), 69(71), 41(80).

f. trans-2,5,6,6-tetramethyl-2-cyclohexene-1-carbaldehyde and
cis-2,5,6,6-tetramethyl-2-cyclohexene-1-carbaldehyde 2.7 Ml of SnCl₄ (23 mmol) were reacted with a solution of 43 g (243.5 mmol) of the epoxide obtained according to example 1e. (94% pure) in 200 ml of toluene. After 5 min, the reaction mixture was neutralized with a saturated solution of NaHCO₃ and then water (100 ml) was added thereto. The aqueous phase was extracted with 2×100 ml of petroleum ether (30°-50°) and the organic phase was washed by means of 2.5 ml of water. After drying over $Na_2SO_4$ and evaporating, a raw product was obtained in the form of a colorless oil (41.7 g). This product was distilled on a 12 cm Vigreux column to yield a mixture containing 48% of trans isomer, 43% of cis isomer and 9% of the β isomer of the above-mentioned carbaldehydes, or 2,5,6,6-tetramethyl-1-cyclohexene-1-carbaldehyde.

B.p.: 70°-85°/4×$10^2$ Pa; yield 77%.

The two desired isomers were separated from the cited mixture by gas phase chromatography and presented the following analytical data:

Trans-2,5,6,6-tetramethyl-2-cyclohexene-1-carbaldehyde

IR: 2900, 1718, 1455, 1380 $cm^{-1}$.

NMR($^1$H, 360 MHz): 0.80(s, 3H); 0.89(d, J=7 Hz, 3H); 1.00(s, 3H); 1.59(broad s, 3H); 2.36(d, J=6 Hz, 1H); 5.70(broad s, 1H); 9.57(d, J=6 Hz, 1H) δ ppm.

MS: 166($M^+$, 15), 137(62), 108(52), 95(100), 81(62), 67(37), 55(50), 41(85).

Cis-2,5,6,6-tetramethyl-2-cyclohexene-1-carbaldehyde

IR: 2900, 1718, 1455, 1380 $cm^{-1}$.

NMR($^1$H, 360 MHz): 0.87(d, J=7 Hz, 3H); 0.90(s, 3H); 0.99(s, 3H); 1.63(broad s, 3H); 2.57(broad s, 1H); 5.66(broad s, 1H); 9.64(d, J=5 Hz, 1H) δ ppm.

MS: 166($M^+$, 11), 137(58), 108(52), 95(100), 81(58), 55(55), 41(82).

g. 2,5,6,6-tetramethyl-1-cyclohexene-1-carbaldehyde

Prepared from the mixture of aldehydes described in f. (7 g, 42.17 mmol) in 50 ml of methanol, by reacting with 1 ml of 30% $NaOCH_3$ in methanol (~5.5 mmol). After 20 min, 100 ml of petroleum ether (30°-50°) were added and the mixture was then neutralized with a 10% aqueous solution of HCl. 20 Ml of an aqueous solution saturated with NaCl were added and the mixture was extracted with 4×50 ml of petroleum ether. After washing the organic phase (2×50 ml saturated NaCl), retaking the aqueous phases in 50 ml of petroleum, drying over $Na_2SO_4$, evaporating and bulb-to-bulb distilling (B. p. ~90°/6×$10^2$ Pa), 6.15 g of 97% pure desired product were obtained (yield: 88%).

IR: 2960, 1660, 1375, 1280 $cm^{-1}$.

NMR($^1$H, 360 MHz): 0.91(d, J=7 Hz, 3H); 1.06(s, 3H); 1.22(s, 3H); 2.09(s, 3H); 10.12(s, 1H) δ ppm.

MS: 166($M^+$, 70), 151(63), 148(35), 133(40), 123(48), 109(77), 95(53), 81(100), 41(91).

Odor: camphor, spicy, minty.

h. (−)-(1R, 3S)-2,2,3-trimethyl-6-methylene-1-cyclohexanecarbaldehyde and (1S, 3S)-2,2,3-trimethyl-6-methylene-1-cyclohexanecarbaldehyde and (1S, 3S)-2,2,3-trimethyl-6-methylene-1-cyclohexanecarbaldehyde Prepared starting from epoxide (+) described in example 1f. (0.85 g, 5 mmol) by reacting with 0.06 ml (0.5 mmol) of $SnCl_4$, in toluene (10 ml). After 10 min, the mixture was decanted, washed twice with 15% HCl, once with saturated $NaHCO_3$ and once with water. The reaction product was dried, concentrated and bulb-to-bulb distilled on residues. 0.4 G (84% pure) of an optically active mixture ($[α]^{20}_D$=−18.9°, c=5.7% $CHCl_3$), containing the above-mentioned isomers in a ratio cis/trans=60:40, were obtained.

(−)-(1R, 3S)-2,2,3-trimethyl-6-methylene-1cyclohexanecarbaldehyde

IR: 3100, 2970, 2750, 1725, 1650, 1460 $cm^{-1}$.

NMR($^1$H, 360 MHz): 0.87(d, J=7 Hz, 3H); 0.98(s, 3H); 1.00(s, 3H); 2.54(d, J=5 Hz, 1H); 4.52(s, 1H); 4.93(s, 1H); 9.92(d, J=5 Hz, 1H) δ ppm.

NMR($^{13}$C): 15.35(q); 15.57(q); 27.2(q); 31.6(t); 36.1(t); 38.0(s); 41.7(d); 65.3(d); 109.5(t); 145.2(s); 205.2(d) δ ppm.

MS: 166($M^+$,5), 151(22), 137(18), 133(13), 123(32), 109(46), 95(100), 83(69), 67(31), 55(48), 41(18).

(1S, 3S)-2,2,3-trimethyl-6-methylene-1-cyclohexanecarbaldehyde

IR: 3100, 2970, 2750, 1725, 1650, 1460 $cm^{-1}$.

NMR($^1$H, 360 MHz): 0.80(s, 3H); 0.85(d, 3H); 1.10(s, 3H); 2.73(d, J=4 Hz, 1H); 4.76(s, 1H); 4.93(s, 1H); 9.87(d, J=4 Hz, 1H) δ ppm.

NMR($^{13}$C): 14.95(q); 21.0(q); 26.5(q); 31.3(t); 32.7(t); 37.15(d); 37.7(s); 69.38(d); 113.36(t); 143.1(s); 205.55(d) δ ppm.

MS: 166($M^+$, 3), 151(7), 137(30), 123(21), 109(32), 95(100), 83(35), 81(56), 67(27), 55(36), 41(12).

i. (+)-(1R, 5S)-5-ethyl-2,6,6-trimethyl-2-cyclohexene-1-carbaldehyde and (1S,5S)-5-ethyl-2,6,6-trimethyl-2-cyclohexene-1-carbaldehyde Prepared from 4.7 g (0.026 mol) of the optically active epoxide described in example 1 g., in 20 ml of toluene, by adding 0.03 ml (0.25 mmol) of $SnCl_4$. After the usual treatment and bulb-to-bulb distillation, 4.1 g of a mixture (76% pure) containing 82% of the mentioned cis isomer and 18% of corresponding trans isomer was obtained.

Yield ~87% ; $[α]^{20}_D$=+29.2°.

IR: 1675, 1720, 2710, 2960 $cm^{-1}$.

(+)-(1R,5S)-5-ethyl-2,6,6-trimethyl-2-cyclohexene-1-carbaldehyde

NMR($^1$H, 360 MHz): 0.93(s, 3H); 1.00(s, 3H); 1.63(s, 3H); 2.54(broad s, 1H); 5.69(broad s, 1H); 9.62(d, J=5 Hz, 1H) δ ppm.

MS: 180($M^+$,21), 165(9), 151(69), 133(15), 122(42), 109(84), 95(86), 91(25), 81(35), 69(74), 55(39), 41(100).

(1S,5S)-5-ethyl-2,6,6-trimethyl-2-cyclohexene-1-carbaldehyde

NMR($^1$H, 360 MHz): 0.89(s, 3H); 1.01(s, 3H); 1.59(s, 3H); 2.34(broad d, J=5 Hz, 1H); 5.73(broad s, 1H); 9.56(d, J=5 Hz, 1H) δ ppm.

MS: 180($M^+$, 20), 151(71), 149(65), 122(40), 109(80), 95(88), 41(100).

EXAMPLE 5

Preparation of Aldehydes of Formula (III) from Alcohols (VI)

General Method

A 3-neck vessel, equipped with good stirring, was charged with pyridinium chlorochromate (PCC) in suspension in dichloromethane (dry) and a solution of the appropriate alcohol in dichloromethane (dry) was added dropwise. The reaction mixture was stirred at room temperature for a period of 1 to 2 h and sulfuric ether was added thereto. It was then passed through a column of SiO₂ using ether as eluting agent. The product was then concentrated and distilled in a bulb-to-bulb apparatus to provide a pure product.

The following aldehydes were thus prepared.

a. 2,2,3,6-tetramethyl-3-cyclohexene-1-carbaldehyde

Prepared according to the method described, starting from 15.0 g (70 mmol) of PCC in 150 ml of CH₂Cl₂ and 8.38 g (50 mmol) of cis-2,2,3,6-tetramethyl-3-cyclohexene-1-methanol, obtained as in example 3b., in 50 ml of CH₂Cl₂. After stirring for 1 h, the reaction mixture was treated as described above to yield 6.77 g of the desired aldehyde in the form of a yellow oil (2 isomers, cis-/trans ~9:1).

B.p.: 130°/1.3×10 Pa; yield 82%.
IR: 2990, 1740, 1470 cm⁻¹.
NMR(¹H, 360 MHz): 0.98(d, J=7.2 Hz, 3H); 1.00(s, 3H); 1.14(s, 3H); 1.72(broad s, 3H); 1.60–2.30(m, 4H); 5.46(broad s, 1H); 9.66(d, J=6.5 Hz, 1H) δ ppm.
MS: 166(M⁺, 11), 151(9), 135(22), 126(56), 108(55), 95(82), 81(100), 67(42), 55(36), 41(13).

b. 2,2,6-trimethyl-3-methylene-1-cyclohexanecarbaldehyde

Prepared according to the method described, starting from 13.0 g (0.06 mol) of PCC in 70 ml of CH₂Cl₂ and a solution of 6.45 g (0.038 mol) of 2,2,6-trimethyl-3-methylene-1-cyclohexanemethanol (obtained according to example 3a.) in 30 ml of CH₂Cl₂. After stirring for 2 h and treating as described, 5.58 g of a colorless oil, containing 80% of the desired aldehyde (2 isomers, cis/trans ~9:1) and a secondary product of no interest, were obtained.

B.p.: 130°/5×10² Pa; yield 88%.
IR: 3100, 2950, 1730, 1650, 1460, 900 cm⁻¹.
NMR(¹H, 360 MHz): 0.91(d, J=7.2 Hz, 3H); 1.07(s, 3H); 1.18(s, 3H); 1.49(m, 1H); 1.76(m, 1H); 1.93(t, J=5.4 Hz, 1H); 2.22(m, 1H); 2.39(m, 1H); 2.55(m, 1H); 4.76(s, 1H); 4.99(s, 1H); 9.64(d, J=7.2 Hz, 1H) δ ppm.
NMR(¹³C): 207.8(d); 152.4(s); 108.5(t); 64.2(d); 32.6(t); 32.5(t); 30.5(d); 28.2(q); 26.5(q); 19.6(q) δ ppm.
MS: 166(M⁺, 2), 160(5), 151(11), 145(21), 135(20), 123(52), 109(35), 95(81), 81(100), 67(41), 55(34), 41(17).
Odor: fenchyl, mouldy, ambrinol.

EXAMPLE 6

Preparation of Ketones of Formula (I)

General Method

The method for preparing ketones of formula (I) and their racemic or optically active isomeric forms, starting from the aldehydes described in examples 4 and 5, may be schematically illustrated as follows:

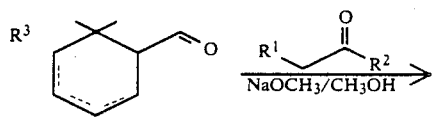

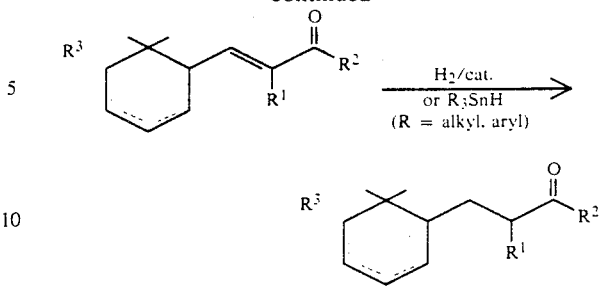

The first step in the represented process consists of an aldol condensation under the following conditions.

A vessel kept under nitrogen was charged with the appropriate carbaldehyde (III) in methanol or ethanol. The mixture was heated to 50° and sodium methylate in methanol (30%) was added to it, followed by the appropriate ketone. The reaction was allowed to proceed for ~20 h at this temperature (the reaction temperature and duration could vary from case to case). The reaction mixture was allowed to cool and neutralized. After extraction with ether, washing to neutrality, drying and concentrating, the raw product was distilled. When necessary, a further purification by chromatography was carried out.

The second step in the process above, if it is a conventional hydrogenation, is carried out in the following conditions.

A vessel equipped with an hydrogenation head was charged with 1 eq./g of unsaturated ketone, 10 eq./g of ethyl acetate and 0.5 g/mol of 10% Pd/C, and a flow of hydrogen was passed therethrough. The reaction product was filtered and concentrated.

An example of a reduction reaction by means of a trialkyltin hydride, which may also constitute this second step, is given under p.

As it has been previously mentioned, the ketones of formula (I) possessing a saturated ring can be prepared in one pot by reacting an epoxide (II) with magnesium iodide, followed by an aldolic condensation such as described above, without separating the intermediate aldehyde. This method is illustrated below under a.

The following ketones were prepared.

a. (E)-4-(2,2,c-3,t-6-tetramethyl-r-1-cyclohexyl)-3-buten-2-one

This compound was prepared in 1 pot, starting from 4,4,t-5,r-8-tetramethyl-1-oxaspiro[2.5]octane obtained according to example 1d. A flask under nitrogen was charged with 1.3 g (54.2 mmol) of magnesium and 12.8 g (50.4 mmol) of iodine in 60 ml of THF. The mixture was stirred for 4 h, maintaining the temperature at 45°, and then the solvent was evaporated at reduced pressure and at the same temperature. After re-establishing the pressure with N₂, 90 ml of dry toluene were introduced, the mixture was heated to reflux and 60 g (357 mmol) of the above-mentioned epoxide were added. After 1½ h, 100 ml of a 30% solution of NaOCH₃ in methanol were slowly added and the mixture was allowed to cool down to 50°. 60 Ml (817 mmol) of acetone were added and the mixture was stirred for 15 h (overnight). After cooling down to 5°, the reaction mixture was diluted with 100 ml of toluene, neutralized with a 15% aqueous solution of HCl, separated, the aqueous phase was separated by means of 15 ml of toluene and the product was dried over MgSO$_4$ and concentrated. Distillation on residues provided 49.4 g of the desired enone (89% pure).

A further distillation on Vigreux column (12 cm) of this product yielded 24 g of a 97.4% pure product.

B.p.: 62°/1.33 Pa; yield 56%.

IR: 2980, 1670, 1620, 1450, 1355, 1250 cm$^{-1}$.

NMR($^1$H, 360 MHz): 0.74(d, J=7 Hz, 3H); 0.76(s, 3H); 0.83(s, 3H); 0.85(d, J=7 Hz, 3H); 2.26(s, 3H); 6.30(d, J=16 Hz, 1H); 6.62(dd, J$_1$=16 Hz, J$_2$=10 Hz, 1H) δ ppm.

MS: 208(M$^+$, 10), 193(6), 175(8), 165(14), 150(19), 111(43), 95(31), 81(31), 55(40), 43(100).

One of the optically active enantiomers of this ketone, i.e., (+)-(1R,3S,6S)-4-(2,2,3,6-tetramethyl-1-cyclohexyl)-3-buten-1-one, was prepared by aldol condensation with acetone of the optically active aldehyde described in example 4b. This optically active ketone, which contained 6% of its (1S,3S,6S) diastereomer, had: [α]$^{20}_D$= +28.15°, c=0.6% CHCl$_3$.

Odor: described in the introduction.

b.
(E)-4-methyl-1-(2,2,c-3,t-6-tetramethyl-r-1-cyclohexyl)-1-penten-3-one

Prepared according to the described general method of aldol condensation, starting form 16 g (0.07 mol) of 2,2,c-3,t-6-tetramethyl-r-1-cyclohexanecarbaldehyde (obtained according to example 4b.) and 20 g (0.023 mol) of di-isopropyl methyl ketone. After fractional distillation, the following two fractions were isolated:
fraction ① 4.2 g ~88% of the desired enone
fraction ② 7.9 g ~96% of the desired enone
B.p.: 53°/5 Pa; yield ~64%.

IR: 1625, 1670, 1695 cm$^{-1}$.

NMR($^1$H, 360 MHz): 0.73(d, J~7 Hz, 3H); 0.76(s, 3H); 0.82(s, 3H); 0.85(d, J~7 Hz, 3H); 1.13(d, J=7 Hz, 6H); 2.86(hept, J=7 Hz, 1H); 6.09(d, J~15 Hz, 1H); 6.68(dd, J$_1$=15 Hz, J$_2$=8 Hz, 1H) δ ppm.

MS: 236(M$^+$, 2), 193(30), 165(14), 150(25), 139(41), 123(34), 109(83), 95(100), 81(70), 69(47), 55(77), 43(61).

Odor: woody, irones.

c.
4-methyl-1-(2,2,c-3,t-6-tetramethyl-r-1-cyclohexyl)-3-pentanone

Prepared by hydrogenation of the enone described under b. (2.7 g, 0.01 mol). After distillation on a rotating band column, 3.3 g of the above-mentioned pentanone, 95% pure.

B.p.: 53°/10.6 Pa; yield ~87%.

IR: 1710 cm$^{-1}$ (C=O).

NMR($^1$H, 360 MHz): 0.66(s, 3H); 0.81(d, J~7 Hz, 3H); 0.87(d, J~7 Hz, 3H); 0.88(s, 3H); 1.10(d, J=7 Hz, 6H); 2.40(m, 1H); 2.55(m, 2H) δ ppm.

MS: 238(M$^+$, 10), 195(15), 177(31), 152(33), 137(43), 121(30), 109(48), 97(65), 83(100), 71(88), 55(87), 43(95).

Odor: camphoraceous, slightly woody.

d.
(E)-2-methyl-1-(2,2,c-3,t-6-tetramethyl-r-1-cyclohexyl)-1-penten-3-one

Prepared by aldol condensation of 16.8 g (0.1 mol) of 2,2,c-3,t-6-tetramethyl-r-1-cyclohexanecarbaldehyde (see example 4b.) and 25.8 g (0.3 mol) of 3-pentanone. The reaction mixture was heated to 65° for 90 h. After distillation on a Vigreux column (10 cm), 9 g of the desired enone, 98% pure, were isolated.

B.p.: 49°/3.5 Pa; yield ~36%; M.p. 45°-51°.

IR: 1640–1660 cm$^{-1}$ (C=O).

NMR($^1$H, 360 MHz): 0.72(d, J~7 Hz, 3H); 0.77(s, 3H); 0.80(s, 3H); 0.85(d, J~6 Hz, 3H); 1.12(t, J~7 Hz, 3H); 1.79(s, 3H); 2.42(q, J=7 Hz, 2H); 6.50(d, J~11 Hz, 1H) δ ppm.

MS: 236(M$^+$, 8), 193(11), 150(27), 137(100), 123(90), 109(68), 99(23), 95(63), 83(48), 69(25), 57(61), 43(32).

Odor: woody, rather weak.

e.
(E)-4-methyl-1-(2,2,c-3,t-6-tetramethyl-r-1-cyclohexyl)-1-hexen-3-one

Prepared by aldol condensation of 15.0 g (89 mmol) of 2,2,c-3,t-6-tetramethyl-r-1-cyclohexanecarbaldehyde in 25 ml of methanol and 20.5 g (205 mmol) of 3-methyl-2-pentanone. The reaction was carried out at 50° and 41.3 ml (223 mmol) of CH$_3$ONa 5.4M in methanol were used. After the usual treatment and distillation in a Vigreux column (20 cm), 17.1 g of a 94% pure product were obtained, consisting in a mixture of the abovementioned hexenone (93%) and its (t-3,c-6) isomer (7%).

B.p.: 75°/1 Pa; yield 72%.

IR: 2960, 2940, 1700, 1625, 1460, 1200, 1000 cm$^{-1}$.

NMR($^1$H, 360 MHz): 0.73(d, J=7 Hz, 3H); 0.76(s, 3H); 0.82(s, 3H); 0.85(d, J=7 Hz, 3H); 0.89(t, J=7 Hz, 3H); 1.1(d, J=7 Hz, 3H); 0.9–1.75(m, 9H); 2.7(m, 1H); 6.1(d, J=18 Hz, 1H); 6.68(d×d, J$_1$=8, J$_2$=18 Hz, 1H) δ ppm.

MS: 250(M$^+$, 4), 207(6), 193(33), 153(26), 123(30), 109(83), 95(100), 81(65), 57(81).

t-3,c-6 isomer

MS: 250(M$^+$, 2), 207(4), 193(28), 151(29), 123(29), 109(71), 95(92), 81(60), 67(43), 55(100).

Odor: mouldy, floral, ambrinol.

f.
(E)-1-(2,2,c-3,t-6-tetramethyl-r-1-cyclohexyl)-1-penten-3-one

Prepared by aldol condensation of 16.8 g (0.1 mol) of 2,2,c-3,t-6-tetramethyl-r-1-cyclohexanecarbaldehyde and 22 g (0.3 mol) of methylethyl ketone. After vacuum distillation of the heads and distillation on residues, two fractions were obtained, as follows:
fraction ① 9.2 g of desired enone 88% pure
fraction ② 3.3 g of desired enone 94% pure
B.p.: 60°/5 Pa; yield ~70%.

IR: 1620–1670 cm$^{-1}$ (C=O).

NMR($^1$H, 360 MHz): 0.73(d, J~7 Hz, 3H); 0.75(s, 3H); 0.82(s, 3H); 0.84(d, J~7 Hz, 3H); 1.11(t, J~7 Hz, 3H); 2.58(q, J=7 Hz, 2H); 6.04(d, J~15 Hz, 1H); 6.64(dd, J$_1$=15 Hz, J$_2$=8 Hz, 1H) δ ppm.

MS: 222(M$^+$, 6), 193(11), 179(11), 165(12), 150(32), 138(27), 123(98), 109(57), 95(79), 81(100), 69(30), 55(99), 41(49).

isomer t-3,t-6

MS: 22(M$^+$, 6), 193(18), 175(14), 165(11), 150(35), 138(27), 123(100), 109(48), 95(65), 81(65), 69(27), 55(52).

Odor: mouldy, earthy, humus.

g.
(E)-4-(2,2,t-3,t-6-tetramethyl-r-1-cyclohexyl)-3-buten-2-one

This compound was prepared by aldol condensation starting from 1.5 g (9 mmol) of 2,2,t-3,t-6-tetramethyl-1- cyclohexanecarbaldehyde [prepared as described by K. H. Schulte-Elte et al. in Helv. Chem. Acta 68, 1961 (1985)] in 10 ml of methanol, 2.5 ml of 5.4M sodium methylate in methanol and 2 ml of acetone. After reacting for 24 h, a further 2.5 ml of 5.4M sodium methylate and 0.7 ml of acetone were added. 48 H later, the reaction product was extracted and treated in the usual manner to yield 2.4 g of raw product. The latter was distilled in a bulb-to-bulb apparatus (B.p. 110°/2.1×10 Pa) to give 1.6 g of the pure desired enone (yield: 86%).

IR: 2950, 1670, 1620, 1450, 1380, 1250, 905 cm$^{-1}$.

NMR($^1$H, 360 MHz): 0.75(d, J=7 Hz, 3H); 0.78(s, 3H); 0.94(d, J=7 Hz, 3H); 1.0(s, 3H); 2.26(s, 3H); 6.3(d, J=18 Hz, 1H); 6.6(dd, J$_1$=18 Hz, J$_2$=8 Hz, 1H) δ ppm.

NMR($^{13}$C): 14.67(q); 21.54(q); 23.73(q); 27.05(q); 28.6(q); 28.6(t); 29.0(t); 31.55(d); 36.1(s); 39.53(d); 52.45(d); 135.14(d); 150.37(d); 198.23(s) δ ppm.

MS: 208(M$^+$, 5), 193(5), 175(7), 165(9), 150(19), 137(12), 124(23), 111(70), 95(65), 81(58), 55(47), 42(100).

Odor: described in the introduction.

h.
(E)-1-(2,2,c-3,t-6-tetramethyl-r-1-cyclohexyl)-1-hepten-3-one

Prepared by aldol condensation of 16.6 g (0.1 mol) of 2,2,c-3,t-6-tetramethyl-r-1-cyclohexanecarbaldehyde and 23.0 g (0.23 mol) of 2-hexanone. After fractional distillation, two fractions containing the desired heptone were obtained:

- fraction ① 3.9 g, 90% pure
- fraction ② 14.2 g, 97% pure

B.p.: 62°/3 Pa; yield 70%.

IR: 1625, 1670 cm$^{-1}$ (C=O).

NMR($^1$H, 360 MHz): 0.73(d, J~7 Hz, 3H); 0.755(s, 3H); 0.82(s, 3H); 0.85(d, J~7 Hz, 3H); 0.93(t, J~7 Hz, 3H); 2.55(t, J~7 Hz, 2H); 6.04(d, J~15 Hz, 1H); 6.63(dd, J$_1$=15 Hz, J$_2$=8 Hz, 2H) δ ppm.

MS: 250(M$^+$, 1), 153(32), 135(16), 123(29), 109(71), 95(92), 85(75), 81(100), 67(35), 55(65), 41(30).

i. trans,
(E)-4-(2,2,6-trimethyl-3-methylene-1-cyclohexyl)-3-buten-2-one

This enone was prepared by reacting 7 g (0.042 mol) of 2,2,3,6-trimethyl-3-methylene-1-cyclohexanecarbaldehyde (prepared as in example 5b.) in 15 ml of ethanol, with 9.3 ml of sodium methylate (30%) and 0.08 mol of acetone. The mixture was stirred for 24 h at room temperature. After the usual treatment, the product was distilled in a bulb-to-bulb apparatus (150°/5×10 Pa) and subjected to a flash-chromatography (cyclohexane/acetic ether: 95:5). 2.26 G of the desired enone, in a pure state (yield 26%) were thus obtained.

IR: 3100, 2950, 1660, 1250, 1000, 900 cm$^{-1}$.

NMR($^1$H, 360 MHz): 0.77(d, J=7.2 Hz, 3H); 1.02(s, 3H); 1.04(s, 3H); 0.98-1.12(m, 1H); 1.61(m, 1H); 1.70-1.90(m, 2H); 2.19(m, 1H); 2.27(s, 3H); 2.37(m, 1H); 4.67(s, 1H); 4.69(s, 1H); 6.04(d, J=16.2 Hz, 1H); 6.62(dd, J$_1$=10.8 Hz, J$_2$=16.2 Hz, 1H) δ ppm.

NMR($^{13}$C): 198(s); 156.1(s); 148.9(d); 133.6(d); 105.8(t); 59.3(d); 39.2(s); 36.6(t); 32.7(t); 31.8(d); 27.2(q); 26.9(q); 21.1(q); 21.2(q) δ ppm.

MS: 206(M$^+$, 5), 188(2), 173(7), 163(9), 148(25), 136(20), 121(36), 109(43), 93(43), 81(100), 71(19), 67(41), 55(47), 43(80).

Odor: described in the introduction.

j. trans,
(E)-1-(2,2,6-trimethyl-3-methylene-1-cyclohexyl)-1-penten-3-one

Prepared in identical manner to that described in i., but replacing acetone by 2-butanone.

IR: 3100, 2950, 1680, 1620, 1460, 1200, 900 cm$^{-1}$.

NMR($^1$H, 360 MHz): 0.76(d, J=7.2 Hz, 3H); 1.02(s, 3H); 1.04(s, 3H); 1.12(t, J=7.2 Hz, 3H); 1.52-1.91(m, 3H); 2.19(m, 1H); 2.37(m, 1H); 2.59(q, J=7.2 Hz, 2H); 4.66(s, 1H); 4.68(s, 1H); 6.04(d, J=15 Hz, 1H); 6.65(dd, J$_1$=10 Hz, J$_2$=15 Hz, 1H) δ ppm.

NMR($^{13}$C): 200.6(s); 156.2(s); 147.6(d); 132.5(d); 105.7(t); 59.3(d); 39.2(s); 36.6(t); 33.6(t); 32.7(t); 31.8(d); 26.9(q); 22.1(q); 21.3(q); 8.3(q) δ ppm.

MS: 220(M$^+$, 9), 205(5), 187(9), 173(7), 163(17), 148(37), 136(33), 121(53), 107(64), 81(100), 67(46), 57(82).

Odor: described in the introduction.

k. trans,
(E)-4-(2,2,3,6-tetramethyl-3-cyclohexen-1-yl)-3-buten-2-one and cis,
(E)-4-(2,2,3,6-tetramethyl-3-cyclohexen-1-yl)-3-buten-2-one The synthesis was carried out following the method described in i. but starting from 2,2,3,6-tetramethyl-3-cyclohexen-1-carbaldehyde obtained according to example 5a. 43 G (yield 50%) of a mixture, containing 58% of trans isomer and 42% of cis isomer of the above-mentioned enone, were obtained. These two isomers were then separated by gas phase chromatography (Carbowax column 5 m). The respective analytical data and olfactive properties were the following:

trans,
(E)-4-(2,2,3,6-tetramethyl-3-cyclohexen-1-yl)-3-buten-2-one

IR: 2950, 1680, 1360, 1250, 1000 cm$^{-1}$.

NMR($^1$H, 360 MHz): 0.80(d, J=7.2 Hz, 3H); 0.95(s, 3H); 0.98(s, 3H); 1.59-1.70(m, 1H); 1.66(broad s, 3H); 1.82(m, 2H); 2.10(m, 1H); 2.28(s, 3H); 5.33(m, 1H); 6.07(d, J=16 Hz, 1H); 6.69(dd, J$_1$=10.8 Hz, J$_2$=16 Hz, 1H) δ ppm.

NMR($^{13}$C): 198.0(s); 149.7(d); 140.4(s); 133.6(d); 121.2(d); 56.7(d); 38.4(s); 34.7(t); 28.3(d); 27.1(q); 26.4(q); 22.1(q); 20.9(q); 18.9(q) δ ppm.

MS: 206(M$^+$, 1), 188(1), 163(3), 122(3), 111(26), 96(100), 81(60), 67(6), 55(7), 43(28).

Odor: described in the introduction.

cis,
(E)-4-(2,2,3,6-tetramethyl-3-cyclohexen-1-yl)-3-buten-2-one

IR: 2950, 1670, 1460, 1360, 1260 cm$^{-1}$.

NMR($^1$H, 360 MHz): 0.84(d, J=7.2 Hz, 3H); 0.88(s, 3H); 1.13(s, 3H); 1.56-1.67(m, 1H); 1.66(broad s, 3H); 1.98(m, 2H); 2.15-2.30(m, 1H); 2.24(s, 3H); 5.36(m, 1H); 6.07(d, J=16 Hz, 1H); 6.62(dd, J$_1$=10.8 Hz, J$_2$=16 Hz, 1H) δ ppm.

NMR($^{13}$C): 198.0(s); 148.1(d); 139.0(s); 133.8(d); 121.1(d); 56.1(d); 37.9(s); 31.1(t); 29.0(q); 28.2(d); 26.8(2q); 20.0(q); 19.0(q) δ ppm.

MS: 206(M$^+$, 2), 149(3), 136(4), 121(9), 111(18), 96(100), 91(100), 81(78), 67(9), 55(9), 43(12).

Odor: irone, violet, slightly fruity. Base note lactonic, dry.

l. trans,(E)-1-(2,2,3,6-tetramethyl-3-cyclohexen-1-yl)-1-penten-3-one and cis,(E)-1-(2,2,3,6-tetramethyl-3-cyclohexen-1-yl)-1-penten-3-one The method described in k. was used with 2-butanone as reagent. 4.8 G of a pure mixture, containing 60% of trans isomer and 40% of cis isomer of the above-mentioned pentenone, were obtained. The two isomers were separated as described in k. Their analytical data and olfactive properties were the following:

trans,(E)-1-(2,2,3,6-tetramethyl-3-cyclohexen-1-yl)-1-penten-3-one

IR: 2970, 1680, 1460, 1360, 1200, 1000 cm$^{-1}$.

NMR($^1$H, 360 MHz): 0.80(d, J=6.5 Hz, 3H); 0.93(s, 3H); 0.97(s, 3H); 1.13(t, J=7.2 Hz, 3H); 1.58–1.71(m, 1H); 1.66(broad s, 3H); 1.80(m, 2H); 2.10(m, 1H); 2.60(q, J=7.2 Hz, 2H); 5.37(m, 1H); 6.08(d, J=15.5 Hz, 1H); 6.72(dd, J$_1$=10.8 Hz, J$_2$=15.5 Hz, 1H) δ ppm.

NMR($^{13}$C): 200.6(s); 148.4(d); 140.4(s); 132.5(d); 121.2(d); 56.7(d); 38.4(s); 34.7(t); 33.4(t); 28.3(d); 26.4(q); 22.1(q); 21.0(q); 19.0(q) δ ppm.

MS: 220(M$^+$, 0), 163(2), 148(2), 125(18), 107(5), 96(100), 91(6), 81(67), 67(9), 57(12), 41(6).

Odor: myrrh, olibanum, sesquiterpene, bisabolene.

cis,(E)-1-(2,2,3,6-tetramethyl-3-cyclohexen-1-yl)-1-penten-3-one

IR: 2950, 1670, 1620, 1460, 1360, 1200, 1000 cm$^{-1}$.

NMR($^1$H, 360 MHz): 0.85(d, J=7.2 Hz, 3H); 0.88(s, 3H); 1.10(t, J=7.2 Hz, 3H); 1.14(s, 3H); 1.60–1.70(m, 1H); 1.64(broad s, 3H); 1.92–2.03(m, 2H); 2.20(m, 1H); 2.57(q, J=7.2 Hz, 2H); 5.35(m, 1H); 6.09(d, J=15.5 Hz, 1H); 6.65(dd, J$_1$=10.8 Hz, J$_2$=15.5 Hz, 1H) δ ppm.

NMR($^{13}$C): 200.9(s); 146.7(d); 139.0(s); 132.7(d); 121.2(d); 56.1(d); 37.7(s); 33.1(t); 31.2(t); 29.0(q); 28.2(d); 26.8(q); 20.0(q); 19.0(q); 8.3(q) δ ppm.

MS: 220(M$^+$, 2), 205(1), 191(1), 163(3), 148(1), 135(3), 125(15), 107(10), 96(100), 81(68), 67(10), 57(19), 41(7).

Odor: myrrh, resinous.

m. trans,(E)-4-(2,5,6,6-tetramethyl-2-cyclohexen-1-yl)-3-buten-2-one (trans-α-irone), cis,(E)-4-(2,5,6,6-tetramethyl-2-cyclohexen-1-yl)-3-buten-2-one (cis-α-irone) and (E)-4-(2,5,6,6-tetramethyl-2-cyclohexen-1-yl)-3-buten-2-one (β-irone)

A mixture of the three above-mentioned irones was prepared starting from a mixture of the aldehydes described in examples 4f. and 4g. This starting mixture (19 g, 114.4 mmol), containing 48% of trans-2,5,6,6-tetramethyl-2-cyclohexen-1-carbaldehyde, 43% of the corresponding cis isomer and 9% of 2,5,6,6-tetramethyl-1-cyclohexen-1-carbaldehyde, dissolved in 10 ml of ethanol, was subjected to an aldol condensation, according to the general method described, with 20 ml of acetone (272.4 mmol) and 1 ml of 30% NaOCH$_3$ in methanol (~5.5 mmol). After reacting for 48 h at room temperature and the usual treatment of the organic phase, 28.3 g of a yellow oil were obtained. These were purified by distillation on a Vigreux column (12 cm) to provide three fractions as follows:

head: 2.4 g of a mixture (81% pure) containing 52% of β-irone, 43% of trans-α-irone and 5% of cis-α-irone main: 13.3 g of a mixture (97% pure) containing 78% of β-irone, 14% of trans-α-irone and 5% of cis-α-irone tail: 3.79 g of 94% pure β-irone.

On the other hand, addition of a solution of 3.0 g (19.74 mmol) of pure 2,5,6,6-tetramethyl-1-cyclohexen-1-carbaldehyde in 3 ml of ethanol and of 3 ml of acetone (41 mmol) to 4 ml (~22 mmol) of a 30% solution of NaOCH$_3$ in methanol, the reaction having proceeded for 18 h at room temperature, provided, after the usual treatment and bulb-to-bulb distillation, a mixture (3.29 g) containing 34% of trans-α-irone, 6% of cis-α-irone and 50% of β-irone (yield 76%).

trans-α-irone

MS: 206(M$^+$, 7), 191(4), 136(51), 121(100), 109(13), 93(68), 43(60).

cis-α-irone

MS: 206(M$^+$, 8), 191(4), 136(50), 121(100), 109(12), 93(68), 43(53).

β-irone

IR: 2900, 1660, 1440, 1355, 1245, 780 cm$^{-1}$.

NMR($^1$H, 360 MHz): 0.91(d, J=7 Hz, 3H); 0.91(s, 3H); 1.06(s, 3H); 1.73(s, 3H); 2.30(s, 3H); 6.07(d, J=16 Hz, 1H); 7.25(d, J=16 Hz, 1H) δ ppm.

MS: 206(M$^+$, 4), 191(100), 149(15), 121(18), 43(52).

n. (E)-1-(2,5,6,6-tetramethyl-1-cyclohexen-1-yl)-1-penten-3-one and (E)-1-(2,5,6,6-tetramethyl-2-cyclohexen-1-yl)-1-penten-3-one These compounds were prepared starting from 5 g (0.03 mol) of trans-2,5,6,6-tetramethyl-2-cyclohexen-1-carbaldehyde (obtained according to example 4f.) and 5.2 g (0.72 mol) of butanone in 20 ml of ethanol. To this mixture there were added 0.3 ml of 30% sodium methylate in methanol and the whole was heated to reflux for 96 h. After the usual treatment and fractional distillation, 2.6 g of a 95% pure mixture were obtained, containing 66.8% of (E)-1-(2,5,6,6-tetramethyl-1-cyclohexen-1-yl)-1-penten-3-one, 27.1% of trans,(E)-1-(2,5,6,6-tetramethyl-2-cyclohexen-1-yl)-1-penten-3-one and 6.1% of cis,(E)-1-(2,5,6,6-tetramethyl-2-cyclohexen-1-yl)-1-penten-3-one.

B.p.: 75°/5 Pa; yield 39%.

IR: 1600, 1670 cm$^{-1}$ (C=O).

NMR($^1$H, 360 MHz):

β-isomer: 0.91(s, 3H); 0.91(d, J=7 Hz, 3H); 1.05(s, 3H); 1.14(t, J=7 Hz, 3H); 1.73(s, 3H); 2.61(q, J=7 Hz, 3H); 6.09(d, J=15 Hz, 1H); 7.28(d, J=15 Hz, 1H) δ ppm.

α-trans isomer: 5.46(broad s, 1H); 6.05(d, J=15 Hz, 1H); 6.71(dd, J$_1$=15 Hz, J$_2$=8 Hz, 1H) δ ppm.

α-cis isomer: 5.52(broad s, 1H); 6.13(d, J=15 Hz, 1H) δ ppm.

MS:

β isomer: 220(M$^+$, 4), 205(100), 163(15), 149(22), 136(15), 121(33), 107(22), 91(27), 77(18), 69(15), 65(10), 57(90), 41(26).

α-trans isomer: 220(M$^+$, 8), 150(44), 135(40), 121(100), 107(10), 93(62), 77(23), 57(52), 41(38).

α-cis isomer: 220(M+, 9), 205(10), 150(53), 135(42), 121(100), 107(10), 93(57), 77(18), 57(30), 41(11).

Odor: methylionone, closer to ionone than to irone.

o.
(−)-(5R,E)-4-(5-ethyl-2,6,6-trimethyl-1-cyclohexen-1-yl)-3-buten-2-one

This compound was prepared by aldol condensation of 2 g (0.011 mol) of (+)-(1R,5S)-5-ethyl-2,6,6-trimethyl-2-cyclohexen-1-carbaldehyde (obtained according to example 4i.) with 2 ml (0.03 mol) of acetone, in 10 ml of ethanol. After adding 0.1 ml of a 30% solution of $CH_3ONa$ in methanol, the reaction was allowed to proceed for about 65 h. Following the usual treatment, 1.3 g of 95% pure mixture were obtained, containing 83% of the above-mentioned butenone, 13% of its α-trans isomer and 4% of its α-cis isomer.

Yield ~56%.

$[\alpha]^{20}_D = -5.6°$.

IR: 1600, 1670 $cm^{-1}$ (C=O).

NMR($^1$H, 360 MHz):

β-isomer: 0.90(s, 3H); 0.94(t, J~4 Hz, 3H); 1.07(s, 3H); 1.74(broad s, 3H); 2.30(s, 3H); 6.07(d, J=15 Hz, 1H); 7.25(d, J=15 Hz, 1H); δ ppm.

α-trans isomer: 1.56(s, 3H); 2.26(s, 3H); 5.50(broad s, 1H); 6.03(d, J=15 Hz, 1H); 6.68(dd, $J_1$=15 Hz, $J_2$=8 Hz, 1H) δ ppm.

α-cis isomer: 5.55(broad s, 1H) δ ppm.

MS:

β isomer: 220(M+, 5), 205(100), 149(15), 135(10), 121(15), 43(57).

α-trans isomer: 220(M+, 21), 136(69), 121(100), 109(12), 93(78), 77(13), 69(14), 55(18), 43(99).

α-cis isomer: 220(M−, 21), 136(100), 121(99), 93(68), 43(60).

Odor: ionones.

p.
4-methyl-1-(2,2,c-3,t-6-tetramethyl-r-1-cyclohexyl)-3-hexanone

This compound was prepared by reduction of the hexenone described in e., according to the following method.

A 4-neck flask equipped with a mechanical stirrer was charged with 11.1 g (44 mmol) of hexenone, 500 ml of toluene and 40.15 g (115 mmol) of triphenyl tin hydride and the mixture was heated to reflux for 6 days (141 h). After cooling down, the reaction product was filtered and concentrated and distilled on residue to give 11.1 g of 96% pure hexanone.

B.p.: 77°/0.5 Pa; yield 95%.

IR: 2960, 1710, 1460, 1370 $cm^{-1}$.

NMR($^1$H, 360 MHz): 0.5(m, 1H); 0.66(s, 3H); 0.82(d, 3H); 0.87(t, J=7 Hz, 3H); 0.88(d, J=7 Hz, 3H); 0.89(s, 3H); 1.06(s, 3H); 1.0–1.4(m, 6H); 1.65(m, 4H); 2.45(m, 3H) δ ppm.

MS: 252(M+, 7), 195(10), 177(20), 152(28), 137(29), 121(20), 109(26), 97(40), 83(63), 69(46), 57(100), 41(53).

Odor: woody, camphoraceous, celluloïd, lavender.

Triphenyl tin hydride was prepared as follows: a 4-neck flask equipped with magnetic stirring was charged with 600 ml of ether and 3.1 g (81 mmol) of $LiAlH_4$ and cooled to 0° (ice+salt bath). 62.6 G (0.16 mol) of triphenyl tin chloride were added by means of a dropping funnel adapted for powder introduction. No exothermic reaction was observed. The mixture was allowed to warm up to room temperature and stirred for 1 h. It was then poured on ice, extracted with ether, washed 3 times with water, dried and concentrated. The raw product thus obtained (56.8 g) was used as such in the synthesis described above.

EXAMPLE 7

Perfuming Composition

A base perfuming composition intended for a feminine type perfume was prepared by admixing the following ingredients:

| Ingredients | Parts by weight |
|---|---|
| Lorol ® [1] | 200 |
| Benzyl acetate | 40 |
| Styrallyl acetate | 120 |
| Vetyveryl acetate | 560 |
| 10%* 10-Undecenal | 80 |
| Hexylcinnamic aldehyde | 80 |
| 10%* Ambrettolide [2] | 100 |
| 1%* Allyl ionone | 80 |
| 1%* γ-Undecalactone | 160 |
| 1%* Raspberry ketone | 80 |
| Cassis Bourgeons absolute | 100 |
| 10%* Coumarin essentail oil | 140 |
| Cyclosia ® [3] base | 500 |
| Galbanum essential oil | 60 |
| Clove bud essential oil | 20 |
| 10%* Isobutyl quinoline [4] | 40 |
| Phenoxyethyl isobutyrate | 20 |
| Jasmin absolute | 240 |
| Levocitrol [5] | 440 |
| Lilial ® [6] | 40 |
| Ethyl linalol | 140 |
| Lyral ® [7] | 260 |
| Iralia ® [8] | 460 |
| 50%* Oakmoss absolute | 320 |
| Hedione ® [9] | 1140 |
| Neroli essential oil | 120 |
| Patchouli essential oil | 40 |
| Phenylethyl alcohol | 760 |
| Portugal sweet orange essential oil | 80 |
| Polywood ® [10] | 160 |
| Marocco rose absolute | 120 |
| Benzyl salicylate | 440 |
| Sandalwood essential oil | 260 |
| Stemone ® [11] | 60 |
| 10%* Tonalid ® [12] | 130 |
| 1%* Vanillin | 50 |
| Vertofix coeur [13] | 1640 |
| Ylang extra | 140 |
| Synthetic hyacinth absolute | 160 |
| Synthetic rose absolute | 320 |
| Total | 9900 |

* in dipropylene glycol (DIPG)
[1] tetrahydro-2-isobutyl-4-methyl-4(2H)-pyranol; origin: Firmenich SA, Geneva, Switzerland
[2] 7-hexadecen-16-olide; origin: L. Givaudan, Geneva, Switzerland
[3] hydroxycitronellal; origin: Firmenich SA, Geneva, Switzerland
[4] 6-(1-methylpropyl)quinoline; origin: International Flavors and Fragrances Inc., USA
[5] levo-citronellol; origin: Firmenich SA, Geneva, Switzerland
[6] 3-(4-tert-butyl-1-phenyl)-2-methylpropanol; origin: L. Givaudan, Geneva, Switzerland
[7] 4-(4-hydroxy-4-methylphenyl)-3-cyclohexene-1-carboxaldehyde; origin: International Flavors & Fragrances Inc., USA
[8] methylionone; origin: Firmenich SA, Geneva, Switzerland
[9] methyl dihydrojasmonate; origin: Firmenich SA, Geneva, Switzerland
[10] perhydro-5,5,8a-trimethyl-2-naphthyl acetate; origin: Firmenich SA, Geneva, Switzerland
[11] 5-methyl-3-heptanone oxime; origin: L. Givaudan, Geneva, Switzerland
[12] 7-acetyl-1,1,3,4,4,6-hexamethyltetraline; origin: PFW, Holland
[13] origin: International Flavors & Fragrances Inc., USA Addition of 1% of (E)-4-(2,2,c-3t-6-tetramethyl-r-1-cyclohexyl)-3-buten-2-one to this base composition of the floral, rosy, jasmine, Chypre type provided a new composition which possessed an iris, balsamic odor note, very powdery and much rounder that the base composition's note. The iris note of the new composition also possessed a more oriental bottom note, the above-mentioned compound according to the invention having brought an olfactive effect reminiscent of that provided by the best quality myrrh essential oils.

EXAMPLE 8

Perfuming Composition

A base perfuming composition intended for a masculine type perfume was prepared by admixing the following ingredients:

| Ingredients | Parts by weight |
| --- | --- |
| Benzyl acetate | 150 |
| Lynalyl acetate | 500 |
| 10%* C10 aldehyde | 150 |
| Synthetic bergamot | 600 |
| Citral pure | 500 |
| Lemon essential oil | 1300 |
| Exaltex ® [1] | 500 |
| Bourbon geranium essentail oil | 550 |
| Lavandin essential oil | 1000 |
| Lilial ® [2] | 200 |
| Coumarin essential oil | 200 |
| Ethyl linalol | 500 |
| Musk ambrette | 500 |
| 10%* Rose oxide [3] | 50 |
| Patchouli essential oil | 850 |
| Petitgrain essential oil | 150 |
| Cedryl acetate | 600 |
| Lynalyl propionate | 150 |
| Amyl salicylate | 100 |
| Benzyl salicylate | 400 |
| 10%* Polysantol ® [4] | 50 |
| Vertofix coeur [5] | 700 |
| Total | 9700 |

* dans le DIPG
[1] pentadecanolide; origin: Firmenich SA, Geneva, Switzerland
[2] see Example 8, under [6]
[3] methylpropenyl methyl tetrahydropyran; origin: Firmenich SA, Geneva, Switzerland
[4] (1'R,E)-3,3-dimethyl-5-(2',2',3',-trimethyl-3'-cylcopenten-1'-yl)-4-penten-2-ol; origin: Firmenich SA, Geneva, Switzerland
[5] see Example 8, under [1]

To this aromatic, woody base composition, there were added 0.3% of the compound according to the invention cited in the previous example. The new composition thus obtained developed an odor the woody note of which was distinctly softened by a floral-violet note, reminiscent of the fragrant effect of the natural violet leaf. Furthermore, the citrus-fresh character of the composition was much more apparent that in the base composition, such that the new composition possessed a more modern connotation.

EXAMPLE 9

Substantivity on Linen 0.1% In weight of the following ingredients were added to a commercial fabric softener in order to prepare four samples A, B, C and D of a perfumed fabric softener:

| Samples | Perfuming Ingredients |
| --- | --- |
| A | α-ionone |
| B | α-methylionone |
| C | α-irone |
| D | (E)-4-(2,2,c-3,t-6-tetramethyl-r-1-cyclohexyl)-3-buten-2-one |

Four standard batches of mixed fabrics, containing each cotton, acrylic and nylon textiles, were separately treated, in four different washing machines, with respectively samples A, B, C and D. The four batches of textiles thus treated were then evaluated in a blind test by a panel of expert perfumers, both when wet and one dried.

The batch of textiles treated with sample D, when wet, developed an odor the impact of which was far stronger than that of the other three batches of textiles.

The results of the comparative evaluations showed that, according to the unanimous opinion of the perfumers, the batch of textiles treated with sample D, which contained (E)-4-(2,2,c-3,t-6-tetramethyl-r-1-cyclohexyl)-3-buten-2-one, developed a much stronger odor than any of the other batches of textiles, when all were just out of the washing machine. In addition, the odor of said batch treated with sample D lasted also far longer after the fabrics were dried. These results show that the compound according to the invention is provided with an odor note of remarkable substantivity, taking into account the fact that all three other perfuming ingredients cited are already well-known for the substantivity of their odor notes.

What we claim is:

1. A compound of formula

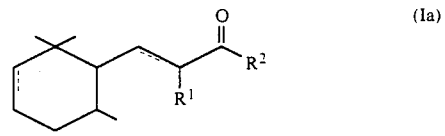

wherein the dotted lines indicate the location of a single or double bond, symbol $R^1$ stands for a hydrogen atom or a methyl radical, symbol $R^2$ represents a linear or branched, saturated or unsaturated, $C_1$ to $C_4$ alkyl radical, with the proviso that $R^1$ cannot be hydrogen when $R^2$ is a methyl or n-propyl radical and the ring is saturated.

2. A compound according to claim 1, essentially as a trans configuration isomer of formula

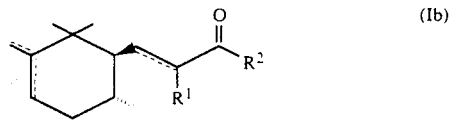

wherein the dotted lines in the ring indicate the location of a double bond, the dotted line in the side chain indicates the location of a single or double bond, symbol $R^1$ stands for a hydrogen atom or a methyl radical and symbol $R^2$ represents a linear or branched, saturated or unsaturated, $C_1$ to $C_4$ alkyl radical, in the form of a racemate or of any one of its optically active enantiomers.

3. A compound according to claim 1, essentially as a trans configuration isomer of formula

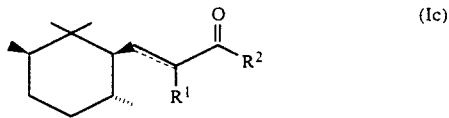

wherein the dotted line indicates the location of a single or double bond and symbols $R^1$ and $R^2$ are defined as in claim 2, in the form of a racemate or of any one of its optically active enantiomers, with the proviso that $R^1$ cannot be hydrogen when $R^2$ is a methyl radical and both the ring and the side chain are saturated.

4. As the compound according to claim 2, any one of the compounds of the following group:

a. trans, (E)-4-(2,2,3,6-tetramethyl-3-cyclohexen-1-yl)-3-buten-2-one,
b. trans, (E)-4-(2,2,6-trimethyl-3-methylene-1-cyclohexyl)-3-buten-2-one,
c. trans, (E)-1-(2,2,6-trimethyl-3-methylene-1-cyclohexyl)-1-penten-3-one in the form of a racemate or of any one of its optically active enantiomers.

5. As the compound according to claim 3, (E)-4-(2,2,c-3,t-6-tetramethyl-r-1-cyclohexyl)-3-buten-2-one in the form of a racemate or of any one of its optically active enantiomers.

6. Trans, (E)-4-(2,2,3,6-tetramethyl-3-cyclohexen-1-yl)-3-buten-2-one; trans, (E)-4-(2,2,6-trimethyl-3-methylene-1-cyclohexyl)-3-buten-2-one; trans, (E)-1-(2,2,6-trimethyl-3-methylene-1-cyclohexyl)-1-penten-3-one; or (E)-4-(2,2,c-3,t-6-tetramethyl-r-1-cyclohexyl)-3-buten-2-one in the form of a racemate or an optically active enantiomer thereof.

* * * * *

UNITED STATES PATENT AND TRADEMARK OFFICE
CERTIFICATE OF CORRECTION

PATENT NO. : 5,118,865

DATED : June 2, 1992

INVENTOR(S) : Christian Chapius et al

It is certified that error appears in the above-identified patent and that said Letters Patent is hereby corrected as shown below:

In the abstract: replace formula Ia with

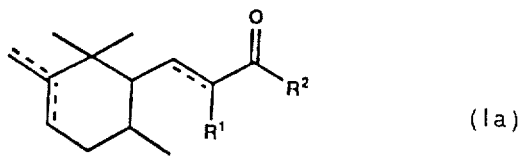
(Ia)

At Column 1, line 15: replace formula Ia with

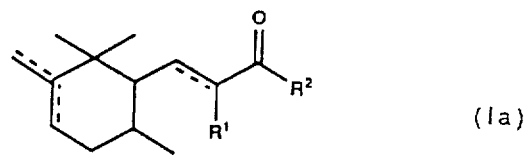
(Ia)

At Column 1, line 40: replace formula Ia with

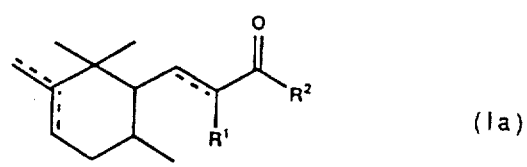
(Ia)

UNITED STATES PATENT AND TRADEMARK OFFICE
CERTIFICATE OF CORRECTION

PATENT NO. : 5,118,865
DATED : June 2, 1992
INVENTOR(S) : Christian Chapius et al It is certified that error appears in the above-identified patent and that said Letters Patent is hereby corrected as shown below:

At Column 2, line 5: replace formula II with

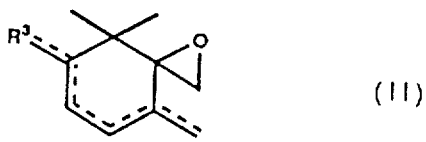

(II)

At Column 2, line 15: replace formula III with

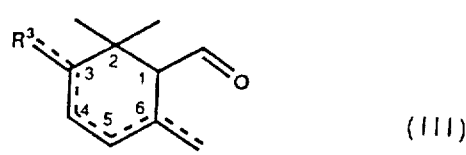

(III)

At Column 6, line 55: replace formula Ib with

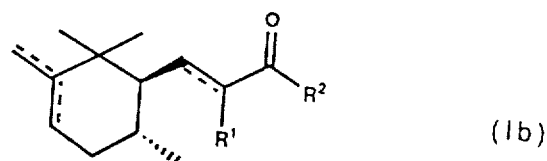

(Ib)

At Column 7, line 4: replace formula IIb with

(IIb)

At Column 7, line 28: replace formula IIc with

(IIc)

UNITED STATES PATENT AND TRADEMARK OFFICE
CERTIFICATE OF CORRECTION

PATENT NO. : 5,118,865

DATED : June 2, 1992

INVENTOR(S) : Christian Chapius et al

Page 3 of 7

It is certified that error appears in the above-identified patent and that said Letters Patent is hereby corrected as shown below:

At Column 7, line 39, replace formula IIIa with

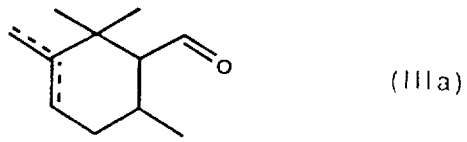

(IIIa)

At Column 7, line 50: replace formula IId with

(IId)

At Column 8, line 9: replace formula IIIc with

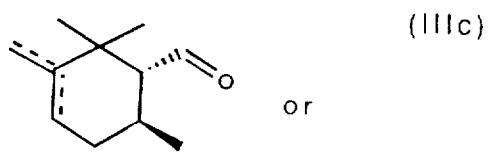

(IIIc)

or

At Column 8, line 14: replace formula IIId with

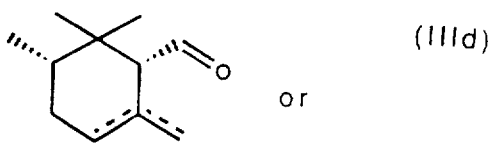

(IIId)

or

UNITED STATES PATENT AND TRADEMARK OFFICE
CERTIFICATE OF CORRECTION

PATENT NO. : 5,118,865

DATED : June 2, 1992

INVENTOR(S) : Christian Chapius et al

It is certified that error appears in the above-identified patent and that said Letters Patent is hereby corrected as shown below:

At Column 8, line 20: replace formula IIIe with

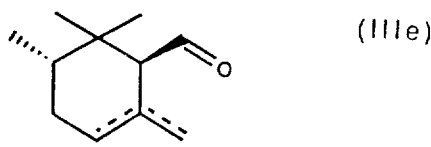

At Column 8, line 45: replace formula VI with

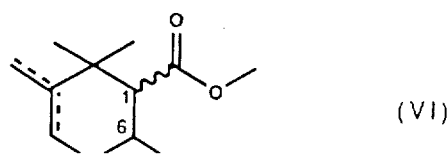

At Column 8, line 59: replace formula VII with

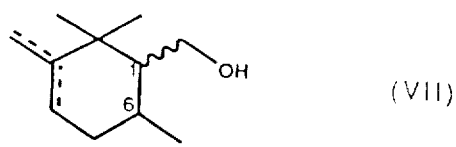

At Column 9, line 2: replace formula III a with

UNITED STATES PATENT AND TRADEMARK OFFICE
CERTIFICATE OF CORRECTION

PATENT NO. : 5,118,865

DATED : June 2, 1992

INVENTOR(S) : Christian Chapius et al

It is certified that error appears in the above-identified patent and that said Letters Patent is hereby corrected as shown below:

At Column 13, line 8: replace formula V with

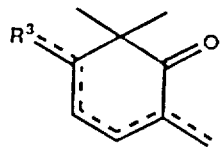

(V)

At Column 13, line 8: replace formula II with

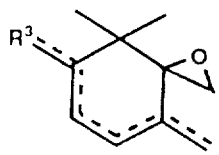

(II)

At Column 18, line 43: replace formula II with

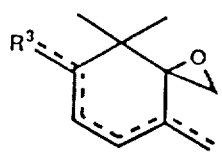

(II)

UNITED STATES PATENT AND TRADEMARK OFFICE
CERTIFICATE OF CORRECTION

PATENT NO. : 5,118,865

DATED : June 2, 1992

INVENTOR(S) : Christian Chapius et al

It is certified that error appears in the above-identified patent and that said Letters Patent is hereby corrected as shown below:

At Column 18, line 44: replace formula III with

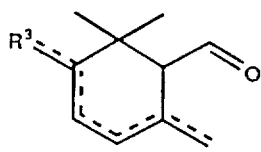

(III)

At Column 21, line 57: delete "and (1S, 3S) -2,2,3 -trimethyl -6-methylene -1- cyclohexanecarbaldehyde"

At Column 23, line 63: replace the figure with

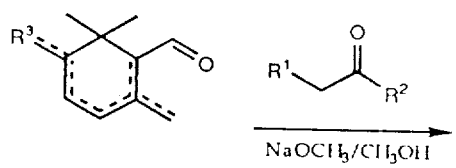

NaOCH$_3$/CH$_3$OH

At Column 24, line 2: replace the figure with

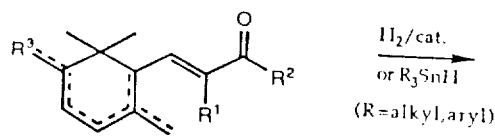

H$_2$/cat.

or R$_3$SnH (R=alkyl,aryl)

At Column 24, line 7: replace the figure with

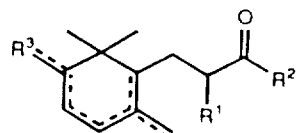

UNITED STATES PATENT AND TRADEMARK OFFICE
CERTIFICATE OF CORRECTION

PATENT NO. : 5,118,865
DATED : June 2, 1992
INVENTOR(S) : Christian Chapius et al It is certified that error appears in the above-identified patent and that said Letters Patent is hereby corrected as shown below:

At Column 32, line 13: replace "Lorol" with -- Florol --.

At Column 34, line 24: replace formula Ia with

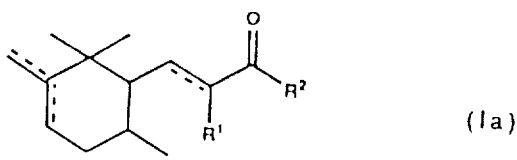

(Ia)

Signed and Sealed this

Fifth Day of October, 1993

*Attest:*

BRUCE LEHMAN

*Attesting Officer*     Commissioner of Patents and Trademarks